US011931026B2

(12) United States Patent
Wise et al.

(10) Patent No.: US 11,931,026 B2
(45) Date of Patent: Mar. 19, 2024

(54) STAPLE CARTRIDGE REPLACEMENT

(71) Applicant: Cilag GmbH International, Zug (CH)

(72) Inventors: Austin E. Wise, Cincinnati, OH (US);
Jeffery D. Bruns, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/363,565

(22) Filed: Jun. 30, 2021

(65) Prior Publication Data

US 2023/0000491 A1 Jan. 5, 2023

(51) Int. Cl.
| | | |
|---|---|---|
| *A61B 17/072* | (2006.01) | |
| *A61B 17/068* | (2006.01) | |
| *A61B 34/30* | (2016.01) | |
| *A61B 17/00* | (2006.01) | |

(52) U.S. Cl.
CPC ........ *A61B 17/072* (2013.01); *A61B 17/0686* (2013.01); *A61B 17/07207* (2013.01); *A61B 34/30* (2016.02); *A61B 2017/00367* (2013.01); *A61B 17/068* (2013.01); *A61B 2017/07214* (2013.01); *A61B 2017/07271* (2013.01)

(58) Field of Classification Search
CPC ............... A61B 17/068; A61B 17/072; A61B 17/07207; A61B 17/115; A61B 17/29; A61B 2017/07214; A61B 2017/07228; A61B 2017/07271; A61B 18/00; A61B 18/1206; A61B 18/1445; A61B 34/35; A61B 34/70; A61B 34/76; A61B 2017/00367; A61B 34/30
USPC ..... 227/19, 176.1, 175.2, 180.1; 606/1, 139, 606/219
See application file for complete search history.

(56) References Cited

U.S. PATENT DOCUMENTS

| | | | |
|---|---|---|---|
| 2,366,274 | A | 1/1945 | Luth et al. |
| 2,458,152 | A | 1/1949 | Eakins |
| 2,510,693 | A | 6/1950 | Green |
| 2,867,039 | A | 1/1959 | Zach |
| 3,166,971 | A | 1/1965 | Stoecker |
| 3,525,912 | A | 8/1970 | Wallin |
| 3,580,841 | A | 5/1971 | Cadotte et al. |
| 3,703,651 | A | 11/1972 | Blowers |

(Continued)

FOREIGN PATENT DOCUMENTS

| | | |
|---|---|---|
| CN | 201223445 Y | 4/2009 |
| CN | 102274074 A | 12/2011 |

(Continued)

OTHER PUBLICATIONS

International Search Report, Application No. PCT/US2013/046777, dated Oct. 1, 2013 (4 pages).

(Continued)

*Primary Examiner* — Scott A Smith

(57) ABSTRACT

A surgical end effector comprising a cartridge jaw is disclosed. The cartridge jaw comprises a proximal channel portion extending along a longitudinal axis, and a distal portion movable relative to the proximal channel portion between an open position and a closed position. The surgical end effector further comprising a staple cartridge removably seated in the cartridge jaw, wherein the staple cartridge is configured to slide along the longitudinal axis into the proximal channel portion of the cartridge jaw when the distal portion is in the open position.

18 Claims, 14 Drawing Sheets

(56) References Cited

U.S. PATENT DOCUMENTS

| | | |
|---|---|---|
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,633,874 A | 1/1987 | Chow et al. |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,910,389 A | 3/1990 | Sherman et al. |
| 4,920,978 A | 5/1990 | Colvin |
| 4,936,842 A | 6/1990 | D'Amelio et al. |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,004 A | 11/1993 | Bales et al. |
| 5,258,006 A | 11/1993 | Rydell et al. |
| 5,285,945 A | 2/1994 | Brinkerhoff et al. |
| 5,290,286 A | 3/1994 | Parins |
| 5,293,863 A | 3/1994 | Zhu et al. |
| 5,309,927 A | 5/1994 | Welch |
| 5,318,564 A | 6/1994 | Eggers |
| 5,318,589 A | 6/1994 | Lichtman |
| 5,330,471 A | 7/1994 | Eggers |
| 5,339,723 A | 8/1994 | Huitema |
| 5,342,359 A | 8/1994 | Rydell |
| 5,361,583 A | 11/1994 | Huitema |
| 5,383,860 A | 1/1995 | Lau |
| 5,383,874 A | 1/1995 | Jackson et al. |
| 5,383,880 A | 1/1995 | Hooven |
| 5,383,888 A | 1/1995 | Zvenyatsky et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,524,643 A | 6/1996 | Faries, Jr. et al. |
| 5,529,235 A | 6/1996 | Boiarski et al. |
| 5,531,744 A | 7/1996 | Nardella et al. |
| 5,542,916 A | 8/1996 | Hirsch et al. |
| 5,558,671 A | 9/1996 | Yates |
| 5,563,179 A | 10/1996 | Stone et al. |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,611,813 A | 3/1997 | Lichtman |
| 5,618,307 A | 4/1997 | Donlon et al. |
| 5,624,452 A | 4/1997 | Yates |
| 5,647,871 A | 7/1997 | Levine et al. |
| 5,658,281 A | 8/1997 | Heard |
| 5,662,615 A | 9/1997 | Blake, III |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,713,896 A | 2/1998 | Nardella |
| 5,716,366 A | 2/1998 | Yates |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,836,909 A | 11/1998 | Cosmescu |
| 5,836,943 A | 11/1998 | Miller, III |
| 5,853,412 A | 12/1998 | Mayenberger |
| 5,876,325 A | 3/1999 | Mizuno et al. |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,980,493 A | 11/1999 | Smith et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| 6,113,598 A | 9/2000 | Baker |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |

(56) References Cited

U.S. PATENT DOCUMENTS

| | | |
|---|---|---|
| 6,174,309 B1 | 1/2001 | Wrublewski et al. |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,241,724 B1 | 6/2001 | Fleischman et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,094 B1 | 5/2002 | Eitenmuller |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,458,130 B1 | 10/2002 | Frazier et al. |
| 6,461,363 B1 | 10/2002 | Gadberry et al. |
| 6,464,702 B2 | 10/2002 | Schulze et al. |
| 6,475,211 B2 | 11/2002 | Chess et al. |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,290 B2 | 3/2003 | Adams et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,709,445 B2 | 3/2004 | Boebel et al. |
| 6,719,765 B2 | 4/2004 | Bonutti |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrodinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,134,587 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,208,005 B2 | 4/2007 | Frecker et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,451,904 B2 | 11/2008 | Shelton, IV |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,491,202 B2 | 2/2009 | Odom et al. |
| 7,494,501 B2 | 2/2009 | Ahlberg et al. |

(56) References Cited

U.S. PATENT DOCUMENTS

| | | |
|---|---|---|
| 7,498,080 B2 | 3/2009 | Tung et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,608,083 B2 | 10/2009 | Lee et al. |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,691,098 B2 | 4/2010 | Wallace et al. |
| 7,703,459 B2 | 4/2010 | Saadat et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,722,527 B2 | 5/2010 | Bouchier et al. |
| 7,722,607 B2 | 5/2010 | Dumbauld et al. |
| 7,727,244 B2 | 6/2010 | Orban, III et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,789,883 B2 | 9/2010 | Takashino et al. |
| 7,803,156 B2 | 9/2010 | Eder et al. |
| 7,806,891 B2 | 10/2010 | Nowlin et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,841,980 B2 | 11/2010 | Minosawa et al. |
| 7,846,159 B2 | 12/2010 | Morrison et al. |
| 7,846,160 B2 | 12/2010 | Payne et al. |
| 7,850,688 B2 | 12/2010 | Hafner |
| 7,867,228 B2 | 1/2011 | Nobis et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,919,184 B2 | 4/2011 | Mohapatra et al. |
| 7,931,649 B2 | 4/2011 | Couture et al. |
| 7,935,114 B2 | 5/2011 | Takashino et al. |
| 7,935,130 B2 | 5/2011 | Williams |
| 7,955,322 B2 | 6/2011 | Devengenzo et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,980,443 B2 | 7/2011 | Scheib et al. |
| 7,981,113 B2 | 7/2011 | Truckai et al. |
| 7,982,776 B2 | 7/2011 | Dunki-Jacobs et al. |
| 7,995,045 B2 | 8/2011 | Dunki-Jacobs |
| 7,997,278 B2 | 8/2011 | Utley et al. |
| 8,016,855 B2 | 9/2011 | Whitman et al. |
| 8,020,743 B2 | 9/2011 | Shelton, IV |
| 8,048,070 B2 | 11/2011 | O'Brien et al. |
| 8,054,184 B2 | 11/2011 | Cline et al. |
| 8,058,771 B2 | 11/2011 | Giordano et al. |
| 8,066,167 B2 | 11/2011 | Measamer et al. |
| 8,070,036 B1 | 12/2011 | Knodel |
| 8,070,731 B2 | 12/2011 | Wenchell et al. |
| 8,075,555 B2 | 12/2011 | Truckai et al. |
| 8,075,558 B2 | 12/2011 | Truckai et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,128,624 B2 | 3/2012 | Couture et al. |
| 8,136,712 B2 | 3/2012 | Zingman |
| 8,141,762 B2 | 3/2012 | Bedi et al. |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,186,560 B2 | 5/2012 | Hess et al. |
| 8,187,267 B2 | 5/2012 | Pappone et al. |
| 8,197,446 B2 | 6/2012 | Beardsley |
| 8,197,472 B2 | 6/2012 | Lau et al. |
| 8,197,479 B2 | 6/2012 | Olson et al. |
| 8,210,411 B2 | 7/2012 | Yates et al. |
| 8,221,415 B2 | 7/2012 | Francischelli |
| 8,241,235 B2 | 8/2012 | Kahler et al. |
| 8,241,283 B2 | 8/2012 | Guerra et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,277,471 B2 | 10/2012 | Wiener et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,232 B2 | 10/2012 | Unger |
| 8,303,583 B2 | 11/2012 | Hosier et al. |
| 8,308,040 B2 | 11/2012 | Huang et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,343,146 B2 | 1/2013 | Godara et al. |
| 8,343,171 B2 | 1/2013 | Farritor et al. |
| 8,348,126 B2 | 1/2013 | Olson et al. |
| 8,357,144 B2 | 1/2013 | Whitman et al. |
| 8,357,158 B2 | 1/2013 | McKenna et al. |
| 8,377,059 B2 | 2/2013 | Deville et al. |
| 8,388,646 B2 | 3/2013 | Chojin |
| 8,397,971 B2 | 3/2013 | Yates et al. |
| 8,403,926 B2 | 3/2013 | Nobis et al. |
| 8,414,577 B2 | 4/2013 | Boudreaux et al. |
| 8,423,182 B2 | 4/2013 | Robinson et al. |
| 8,425,410 B2 | 4/2013 | Murray et al. |
| 8,430,811 B2 | 4/2013 | Hess et al. |
| 8,430,876 B2 | 4/2013 | Kappus et al. |
| 8,453,906 B2 | 6/2013 | Huang et al. |
| 8,454,599 B2 | 6/2013 | Inagaki et al. |
| 8,460,288 B2 | 6/2013 | Tamai et al. |
| 8,460,292 B2 | 6/2013 | Truckai et al. |
| 8,484,833 B2 | 7/2013 | Cunningham et al. |
| 8,485,970 B2 | 7/2013 | Widenhouse et al. |
| 8,486,057 B2 | 7/2013 | Behnke, II |
| 8,491,533 B2 | 7/2013 | Parihar et al. |
| 8,491,625 B2 | 7/2013 | Horner |
| 8,496,682 B2 | 7/2013 | Guerra et al. |
| 8,512,364 B2 | 8/2013 | Kowalski et al. |
| 8,529,437 B2 | 9/2013 | Taylor et al. |

(56) References Cited

U.S. PATENT DOCUMENTS

| | | |
|---|---|---|
| 8,535,311 B2 | 9/2013 | Schall |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,579,176 B2 | 11/2013 | Smith et al. |
| 8,579,937 B2 | 11/2013 | Gresham |
| 8,591,459 B2 | 11/2013 | Clymer et al. |
| 8,591,506 B2 | 11/2013 | Wham et al. |
| 8,613,383 B2 | 12/2013 | Beckman et al. |
| 8,613,727 B2 | 12/2013 | Hart et al. |
| 8,616,431 B2 | 12/2013 | Timm et al. |
| 8,622,274 B2 | 1/2014 | Yates et al. |
| 8,623,016 B2 | 1/2014 | Fischer |
| 8,623,044 B2 | 1/2014 | Timm et al. |
| 8,628,529 B2 | 1/2014 | Aldridge et al. |
| 8,632,461 B2 | 1/2014 | Glossop |
| 8,636,736 B2 | 1/2014 | Yates et al. |
| 8,640,788 B2 | 2/2014 | Dachs, II et al. |
| 8,647,350 B2 | 2/2014 | Mohan et al. |
| 8,652,120 B2 | 2/2014 | Giordano et al. |
| 8,663,222 B2 | 3/2014 | Anderson et al. |
| 8,668,691 B2 | 3/2014 | Heard |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,784,418 B2 | 7/2014 | Romero |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,801,752 B2 | 8/2014 | Fortier et al. |
| 8,814,856 B2 | 8/2014 | Elmouelhi et al. |
| 8,827,995 B2 | 9/2014 | Schaller et al. |
| 8,828,023 B2 | 9/2014 | Neff et al. |
| 8,834,466 B2 | 9/2014 | Cummings et al. |
| 8,834,518 B2 | 9/2014 | Faller et al. |
| 8,851,354 B2 | 10/2014 | Swensgard et al. |
| 8,864,757 B2 | 10/2014 | Klimovitch et al. |
| 8,864,761 B2 | 10/2014 | Johnson et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,912,746 B2 | 12/2014 | Reid et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,961,515 B2 | 2/2015 | Twomey et al. |
| 8,979,843 B2 | 3/2015 | Timm et al. |
| 8,979,844 B2 | 3/2015 | White et al. |
| 8,986,302 B2 | 3/2015 | Aldridge et al. |
| 8,992,422 B2 | 3/2015 | Spivey et al. |
| 8,992,526 B2 | 3/2015 | Brodbeck et al. |
| 9,002,518 B2 | 4/2015 | Manzo et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,333 B2 | 4/2015 | Beale et al. |
| 9,028,494 B2 | 5/2015 | Shelton, IV et al. |
| 9,028,519 B2 | 5/2015 | Yates et al. |
| 9,039,695 B2 | 5/2015 | Giordano et al. |
| 9,039,705 B2 | 5/2015 | Takashino |
| 9,044,243 B2 | 6/2015 | Johnson et al. |
| 9,044,245 B2 | 6/2015 | Condie et al. |
| 9,050,093 B2 | 6/2015 | Aldridge et al. |
| 9,050,098 B2 | 6/2015 | Deville et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,072,535 B2 | 7/2015 | Shelton, IV et al. |
| 9,072,536 B2 | 7/2015 | Shelton, IV et al. |
| 9,089,360 B2 | 7/2015 | Messerly et al. |
| 9,095,362 B2 | 8/2015 | Dachs, II et al. |
| 9,101,385 B2 | 8/2015 | Shelton, IV et al. |
| 9,106,270 B2 | 8/2015 | Puterbaugh et al. |
| 9,107,684 B2 | 8/2015 | Ma |
| 9,113,900 B2 | 8/2015 | Buysse et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,149,324 B2 | 10/2015 | Huang et al. |
| 9,161,803 B2 | 10/2015 | Yates et al. |
| 9,168,054 B2 | 10/2015 | Turner et al. |
| 9,168,089 B2 | 10/2015 | Buysse et al. |
| 9,179,912 B2 | 11/2015 | Yates et al. |
| 9,192,431 B2 | 11/2015 | Woodruff et al. |
| 9,198,715 B2 | 12/2015 | Livneh |
| 9,204,879 B2 | 12/2015 | Shelton, IV |
| 9,220,559 B2 | 12/2015 | Worrell et al. |
| 9,226,751 B2 | 1/2016 | Shelton, IV et al. |
| 9,237,891 B2 | 1/2016 | Shelton, IV |
| 9,254,165 B2 | 2/2016 | Aronow et al. |
| 9,259,265 B2 | 2/2016 | Harris et al. |
| 9,259,277 B2 | 2/2016 | Rogers et al. |
| 9,265,567 B2 | 2/2016 | Orban, III et al. |
| 9,265,926 B2 | 2/2016 | Strobl et al. |
| 9,282,974 B2 | 3/2016 | Shelton, IV |
| 9,283,027 B2 | 3/2016 | Monson et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,320,563 B2 | 4/2016 | Brustad et al. |
| 9,333,025 B2 | 5/2016 | Monson et al. |
| 9,339,323 B2 | 5/2016 | Eder et al. |
| 9,339,342 B2 | 5/2016 | Prisco et al. |
| 9,345,481 B2 | 5/2016 | Hall et al. |
| 9,364,230 B2 | 6/2016 | Shelton, IV et al. |
| 9,375,232 B2 | 6/2016 | Hunt et al. |
| 9,386,983 B2 | 7/2016 | Swensgard et al. |
| 9,402,682 B2 | 8/2016 | Worrell et al. |
| 9,408,606 B2 | 8/2016 | Shelton, IV |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,864 B2 | 10/2016 | Witt et al. |
| 9,492,224 B2 | 11/2016 | Boudreaux et al. |
| 9,504,524 B2 | 11/2016 | Behnke, II |
| 9,526,407 B2 | 12/2016 | Hoeg et al. |
| 9,526,565 B2 | 12/2016 | Strobl |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,572,552 B1 | 2/2017 | Bodor et al. |
| 9,597,104 B2 | 3/2017 | Nicholas et al. |
| 9,597,143 B2 | 3/2017 | Madan et al. |
| 9,610,091 B2 | 4/2017 | Johnson et al. |
| 9,642,669 B2 | 5/2017 | Takashino et al. |
| 9,649,110 B2 | 5/2017 | Parihar et al. |
| 9,649,111 B2 | 5/2017 | Shelton, IV et al. |

(56) References Cited

U.S. PATENT DOCUMENTS

| | | |
|---|---|---|
| 9,668,806 B2 | 6/2017 | Unger et al. |
| 9,707,027 B2 | 7/2017 | Ruddenklau et al. |
| 9,737,355 B2 | 8/2017 | Yates et al. |
| 9,737,358 B2 | 8/2017 | Beckman et al. |
| 9,757,128 B2 | 9/2017 | Baber et al. |
| 9,757,186 B2 | 9/2017 | Boudreaux et al. |
| 9,763,661 B2 | 9/2017 | Zergiebel et al. |
| 9,782,214 B2 | 10/2017 | Houser et al. |
| 9,795,436 B2 | 10/2017 | Yates et al. |
| 9,808,308 B2 | 11/2017 | Faller et al. |
| 9,814,514 B2 | 11/2017 | Shelton, IV et al. |
| 9,820,740 B2 | 11/2017 | Zemlok et al. |
| 9,820,771 B2 | 11/2017 | Norton et al. |
| 9,861,428 B2 | 1/2018 | Trees et al. |
| 9,877,776 B2 | 1/2018 | Boudreaux |
| 9,888,942 B1 | 2/2018 | Savage et al. |
| 9,913,680 B2 | 3/2018 | Voegele et al. |
| 9,913,694 B2 | 3/2018 | Brisson |
| 9,937,626 B2 | 4/2018 | Rockrohr |
| 9,987,008 B2 | 6/2018 | Scirica et al. |
| 10,016,207 B2 | 7/2018 | Suzuki et al. |
| 10,070,916 B2 | 9/2018 | Artale |
| 10,092,310 B2 | 10/2018 | Boudreaux et al. |
| 10,098,527 B2 | 10/2018 | Weisenburgh, II et al. |
| 10,164,466 B2 | 12/2018 | Calderoni |
| 10,166,060 B2 | 1/2019 | Johnson et al. |
| 10,166,080 B2 | 1/2019 | Balicki et al. |
| 10,166,082 B1 | 1/2019 | Hariri et al. |
| 10,172,669 B2 | 1/2019 | Felder et al. |
| 10,172,687 B2 | 1/2019 | Garbus et al. |
| 10,179,413 B2 | 1/2019 | Rockrohr |
| 10,194,976 B2 | 2/2019 | Boudreaux |
| 10,213,266 B2 | 2/2019 | Zemlok et al. |
| 10,231,775 B2 | 3/2019 | Shelton, IV et al. |
| 10,251,672 B2 | 4/2019 | Meglan |
| 10,258,359 B2 | 4/2019 | Kapadia |
| 10,265,118 B2 | 4/2019 | Gerhardt |
| 10,278,721 B2 | 5/2019 | Dietz et al. |
| 10,321,964 B2 | 6/2019 | Grover et al. |
| 10,368,838 B2 | 8/2019 | Williams et al. |
| 10,376,338 B2 | 8/2019 | Taylor et al. |
| 10,390,895 B2 | 8/2019 | Henderson et al. |
| 10,398,517 B2 | 9/2019 | Eckert et al. |
| 10,420,620 B2 | 9/2019 | Rockrohr |
| 10,426,516 B2 | 10/2019 | Racenet et al. |
| 10,463,421 B2 | 11/2019 | Boudreaux et al. |
| 10,470,830 B2 | 11/2019 | Hill et al. |
| 10,507,068 B2 | 12/2019 | Kopp et al. |
| 10,517,686 B2 | 12/2019 | Vokrot et al. |
| 10,537,351 B2 | 1/2020 | Shelton, IV et al. |
| 10,548,504 B2 | 2/2020 | Shelton, IV et al. |
| 10,561,470 B2 | 2/2020 | Hourtash et al. |
| 10,588,706 B2 | 3/2020 | Limon |
| 10,624,691 B2 | 4/2020 | Wiener et al. |
| 10,639,111 B2 | 5/2020 | Kopp |
| 10,653,489 B2 | 5/2020 | Kopp |
| 10,667,877 B2 | 6/2020 | Kapadia |
| 10,675,104 B2 | 6/2020 | Kapadia |
| 10,716,639 B2 | 7/2020 | Kapadia et al. |
| 10,736,219 B2 | 8/2020 | Seow et al. |
| 10,743,872 B2 | 8/2020 | Leimbach et al. |
| 10,751,087 B2 | 8/2020 | Morgan et al. |
| 10,765,484 B2 | 9/2020 | Bonutti et al. |
| 10,772,688 B2 | 9/2020 | Peine et al. |
| 10,779,849 B2 | 9/2020 | Shelton, IV et al. |
| 10,779,897 B2 | 9/2020 | Rockrohr |
| 10,779,900 B2 | 9/2020 | Pedros et al. |
| 10,799,304 B2 | 10/2020 | Kapadia et al. |
| 10,806,454 B2 | 10/2020 | Kopp |
| 10,813,703 B2 | 10/2020 | Swayze et al. |
| 10,849,700 B2 | 12/2020 | Kopp et al. |
| 10,881,399 B2 | 1/2021 | Shelton, IV et al. |
| 10,893,884 B2 | 1/2021 | Stoddard et al. |
| 10,898,280 B2 | 1/2021 | Kopp |
| 10,912,616 B2 | 2/2021 | Dachs, II et al. |
| 10,932,772 B2 | 3/2021 | Shelton, IV et al. |
| 10,959,788 B2 | 3/2021 | Grover et al. |
| 10,980,610 B2 | 4/2021 | Rosenberg et al. |
| 11,013,569 B2 | 5/2021 | Shelton, IV et al. |
| 11,026,764 B2 | 6/2021 | Kopp |
| 11,045,265 B2 | 6/2021 | Seow et al. |
| 11,058,504 B2 | 7/2021 | Blanco et al. |
| 11,090,125 B2 | 8/2021 | Peine et al. |
| 11,109,866 B2 | 9/2021 | Shelton, IV et al. |
| 11,160,623 B2 | 11/2021 | Hagn |
| 11,207,146 B2 | 12/2021 | Shelton, IV et al. |
| 11,229,471 B2 | 1/2022 | Shelton, IV et al. |
| 11,278,362 B2 | 3/2022 | Shelton, IV et al. |
| 11,298,128 B2 | 4/2022 | Messerly et al. |
| 11,304,699 B2 | 4/2022 | Shelton, IV et al. |
| 11,364,067 B2 | 6/2022 | Murrell et al. |
| 11,369,443 B2 | 6/2022 | Shelton, IV et al. |
| 11,376,082 B2 | 7/2022 | Shelton, IV et al. |
| 11,376,083 B2 | 7/2022 | Harris et al. |
| 11,389,164 B2 | 7/2022 | Yates et al. |
| 11,399,906 B2 | 8/2022 | Shelton, IV et al. |
| 11,413,102 B2 | 8/2022 | Shelton, IV et al. |
| 11,432,885 B2 * | 9/2022 | Shelton, IV ............ G16H 20/40 |
| 11,510,747 B2 | 11/2022 | Zemlok et al. |
| 2002/0022836 A1 | 2/2002 | Goble et al. |
| 2002/0072736 A1 | 6/2002 | Tierney et al. |
| 2003/0014053 A1 | 1/2003 | Nguyen et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0229344 A1 | 12/2003 | Dycus et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0249374 A1 | 12/2004 | Tetzlaff et al. |
| 2004/0260273 A1 | 12/2004 | Wan |
| 2005/0006432 A1 | 1/2005 | Racenet et al. |
| 2005/0015125 A1 | 1/2005 | Mioduski et al. |
| 2005/0033278 A1 | 2/2005 | McClurken et al. |
| 2005/0090817 A1 | 4/2005 | Phan |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0267464 A1 | 12/2005 | Truckai et al. |
| 2006/0064086 A1 | 3/2006 | Odom |
| 2006/0069306 A1 | 3/2006 | Banik et al. |
| 2006/0135978 A1 | 6/2006 | Franer |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0032704 A1 | 2/2007 | Gandini et al. |
| 2007/0073185 A1 | 3/2007 | Nakao |
| 2007/0073341 A1 | 3/2007 | Smith et al. |
| 2007/0078395 A1 | 4/2007 | Valaie |
| 2007/0135826 A1 | 6/2007 | Zaver et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0260242 A1 | 11/2007 | Dycus et al. |
| 2007/0265613 A1 | 11/2007 | Edelstein et al. |
| 2007/0282358 A1 | 12/2007 | Remiszewski et al. |
| 2008/0015575 A1 | 1/2008 | Odom et al. |
| 2008/0064921 A1 | 3/2008 | Larkin et al. |
| 2008/0071269 A1 | 3/2008 | Hilario et al. |
| 2008/0081948 A1 | 4/2008 | Weisenburgh et al. |
| 2008/0114355 A1 | 5/2008 | Whayne et al. |
| 2008/0125794 A1 | 5/2008 | Brock et al. |
| 2008/0147058 A1 | 6/2008 | Horrell et al. |
| 2008/0147062 A1 | 6/2008 | Truckai et al. |
| 2008/0188755 A1 | 8/2008 | Hart |
| 2008/0281315 A1 | 11/2008 | Gines |
| 2009/0012516 A1 | 1/2009 | Curtis et al. |

(56) References Cited

U.S. PATENT DOCUMENTS

| | | |
|---|---|---|
| 2009/0048589 A1 | 2/2009 | Takashino et al. |
| 2009/0076506 A1 | 3/2009 | Baker |
| 2009/0182327 A1 | 7/2009 | Unger |
| 2009/0182332 A1 | 7/2009 | Long et al. |
| 2009/0248021 A1 | 10/2009 | McKenna |
| 2009/0248037 A1 | 10/2009 | Prisco |
| 2009/0248041 A1 | 10/2009 | Williams et al. |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0168520 A1 | 7/2010 | Poll et al. |
| 2010/0222752 A1 | 9/2010 | Collins, Jr. et al. |
| 2010/0228264 A1 | 9/2010 | Robinson et al. |
| 2010/0274278 A1 | 10/2010 | Fleenor et al. |
| 2011/0028964 A1 | 2/2011 | Edwards |
| 2011/0230719 A1 | 9/2011 | Katakura et al. |
| 2011/0290856 A1 | 12/2011 | Shelton, IV et al. |
| 2011/0295295 A1 | 12/2011 | Shelton, IV et al. |
| 2011/0301414 A1 | 12/2011 | Hotto et al. |
| 2011/0306840 A1 | 12/2011 | Allen et al. |
| 2011/0306967 A1 | 12/2011 | Payne et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078244 A1 | 3/2012 | Worrell et al. |
| 2012/0109186 A1 | 5/2012 | Parrott et al. |
| 2012/0111920 A1 | 5/2012 | Kostrzewski |
| 2012/0116222 A1 | 5/2012 | Sawada et al. |
| 2012/0116265 A1 | 5/2012 | Houser et al. |
| 2012/0132018 A1 | 5/2012 | Tang et al. |
| 2012/0238827 A1 | 9/2012 | Berry et al. |
| 2012/0303025 A1 | 11/2012 | Garrison |
| 2013/0023915 A1 | 1/2013 | Mueller |
| 2013/0023925 A1 | 1/2013 | Mueller |
| 2013/0085510 A1 | 4/2013 | Stefanchik et al. |
| 2013/0123776 A1 | 5/2013 | Monson et al. |
| 2013/0331730 A1 | 12/2013 | Fenech et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0066944 A1 | 3/2014 | Taylor et al. |
| 2014/0207135 A1 | 7/2014 | Winter |
| 2014/0246477 A1 | 9/2014 | Koch, Jr. et al. |
| 2014/0263552 A1 | 9/2014 | Hall et al. |
| 2014/0276944 A1 | 9/2014 | Farritor et al. |
| 2014/0343569 A1 | 11/2014 | Turner |
| 2014/0371763 A1 | 12/2014 | Poll et al. |
| 2015/0038981 A1 | 2/2015 | Kilroy et al. |
| 2015/0080876 A1 | 3/2015 | Worrell et al. |
| 2015/0114404 A1 | 4/2015 | Czop et al. |
| 2015/0272659 A1 | 10/2015 | Boudreaux et al. |
| 2016/0015261 A1 | 1/2016 | Kishi et al. |
| 2016/0051316 A1 | 2/2016 | Boudreaux |
| 2016/0113728 A1 | 4/2016 | Piron et al. |
| 2016/0175028 A1 | 6/2016 | Trees et al. |
| 2016/0346930 A1 | 12/2016 | Hares |
| 2016/0361122 A1 | 12/2016 | Seeber |
| 2016/0361127 A1 | 12/2016 | Dachs, II et al. |
| 2017/0028562 A1 | 2/2017 | Yamazaki et al. |
| 2017/0079708 A1 | 3/2017 | Gilbert et al. |
| 2017/0079730 A1 | 3/2017 | Azizian et al. |
| 2017/0105785 A1 | 4/2017 | Shelton, IV et al. |
| 2017/0135771 A1 | 5/2017 | Auld et al. |
| 2017/0188802 A1 | 7/2017 | Lawrence et al. |
| 2017/0224428 A1 | 8/2017 | Kopp |
| 2017/0296213 A1 | 10/2017 | Swensgard et al. |
| 2017/0296257 A1 | 10/2017 | Shelton, IV et al. |
| 2017/0333145 A1 | 11/2017 | Griffiths et al. |
| 2018/0085175 A1 | 3/2018 | Steinle et al. |
| 2018/0125568 A1 | 5/2018 | Shelton, IV et al. |
| 2018/0192862 A1 | 7/2018 | Ide |
| 2018/0289427 A1 | 10/2018 | Griffiths et al. |
| 2018/0296286 A1 | 10/2018 | Peine et al. |
| 2019/0000478 A1* | 1/2019 | Messerly ............ A61B 18/1445 |
| 2019/0053866 A1 | 2/2019 | Seow et al. |
| 2019/0059986 A1 | 2/2019 | Shelton, IV et al. |
| 2019/0083182 A1 | 3/2019 | Roach et al. |
| 2019/0094084 A1 | 3/2019 | Swinehart et al. |
| 2019/0104919 A1 | 4/2019 | Shelton, IV et al. |
| 2019/0125457 A1 | 5/2019 | Parihar et al. |
| 2019/0133703 A1 | 5/2019 | Seow et al. |
| 2019/0167267 A1 | 6/2019 | Kobayashi et al. |
| 2019/0183596 A1 | 6/2019 | Dachs, II |
| 2019/0200844 A1 | 7/2019 | Shelton, IV et al. |
| 2019/0200981 A1 | 7/2019 | Harris et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201111 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201142 A1 | 7/2019 | Shelton, IV et al. |
| 2019/0201594 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0298471 A1 | 10/2019 | Holop |
| 2019/0314107 A1 | 10/2019 | Worrell et al. |
| 2019/0321112 A1 | 10/2019 | Cecil |
| 2019/0328469 A1 | 10/2019 | Ando et al. |
| 2019/0357884 A1 | 11/2019 | Williams et al. |
| 2020/0000536 A1 | 1/2020 | Yakimovich et al. |
| 2020/0054412 A1 | 2/2020 | Fuerst et al. |
| 2020/0078109 A1 | 3/2020 | Steger et al. |
| 2020/0093554 A1 | 3/2020 | Schuh et al. |
| 2020/0197108 A1 | 6/2020 | Usui |
| 2020/0214776 A1 | 7/2020 | Hingwe et al. |
| 2020/0246063 A1 | 8/2020 | Shelton, IV et al. |
| 2020/0281675 A1 | 9/2020 | Meglan |
| 2020/0315715 A1 | 10/2020 | Rockrohr et al. |
| 2020/0315721 A1 | 10/2020 | Rabindran et al. |
| 2020/0405375 A1 | 12/2020 | Shelton, IV et al. |
| 2020/0405401 A1 | 12/2020 | Shelton, IV et al. |
| 2020/0405404 A1 | 12/2020 | Shelton, IV et al. |
| 2020/0405408 A1 | 12/2020 | Shelton, IV et al. |
| 2020/0405415 A1 | 12/2020 | Shelton, IV et al. |
| 2020/0405417 A1 | 12/2020 | Shelton, IV et al. |
| 2020/0405421 A1 | 12/2020 | Luck |
| 2021/0015519 A1 | 1/2021 | Meglan et al. |
| 2021/0059777 A1 | 3/2021 | Overmyer et al. |
| 2021/0068889 A1 | 3/2021 | Shelton, IV et al. |
| 2021/0093409 A1 | 4/2021 | Overmyer et al. |
| 2021/0196356 A1 | 7/2021 | Shelton, IV et al. |
| 2021/0212777 A1 | 7/2021 | Cheng |
| 2021/0401524 A1 | 12/2021 | Suresh et al. |
| 2022/0031350 A1 | 2/2022 | Witte |
| 2022/0054208 A1 | 2/2022 | Cooper et al. |
| 2022/0202437 A1 | 6/2022 | Overmyer et al. |
| 2022/0202514 A1 | 6/2022 | Boudreaux |
| 2022/0202517 A1 | 6/2022 | Overmyer et al. |
| 2022/0203519 A1 | 6/2022 | Overmyer et al. |
| 2022/0218407 A1 | 7/2022 | Shelton, IV et al. |
| 2022/0287782 A1 | 9/2022 | Shelton, IV et al. |
| 2023/0000542 A1 | 1/2023 | Murrell |
| 2023/0000578 A1 | 1/2023 | Moubarak |
| 2023/0001579 A1 | 1/2023 | Overmyer et al. |
| 2023/0320776 A1 | 10/2023 | Shelton, IV et al. |

FOREIGN PATENT DOCUMENTS

| | | |
|---|---|---|
| DE | 29623113 U1 | 10/1997 |
| DE | 20004812 U1 | 9/2000 |
| DE | 10201569 A1 | 7/2003 |
| EP | 0705571 A1 | 4/1996 |
| EP | 2060238 A1 | 5/2009 |
| EP | 1747761 B1 | 10/2009 |
| JP | H08229050 A | 9/1996 |
| SU | 578972 A1 | 11/1977 |

(56) References Cited

FOREIGN PATENT DOCUMENTS

| WO | WO-8103272 A1 | 11/1981 |
|---|---|---|
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-2004078051 A2 | 9/2004 |
| WO | WO-2010104755 A1 | 9/2010 |
| WO | WO-2012044606 A2 | 4/2012 |

OTHER PUBLICATIONS

International Preliminary Report on Patentability, Application No. PCT/US2013/046777, dated Dec. 31, 2014 (5 pages).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, Integrated Circuit Engineering, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Jang, J. et al. "Neuro-fuzzy and Soft Computing." Prentice Hall, 1997, pp. 13-89, 199-293, 335-393, 453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Covidien Brochure, The LigaSure Precise™ Instrument, dated Mar. 2011 (2 pages).
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.

\* cited by examiner

STAPLE CARTRIDGE REPLACEMENT

BACKGROUND

The disclosure relates to surgical devices, including robotic surgical tools configured to releasably receive a replaceable staple cartridge therein.

SUMMARY

In one general aspect, the present disclosure provides a surgical end effector, comprising a cartridge jaw. The cartridge jaw comprises a proximal channel portion extending along a longitudinal axis, and a distal portion movable relative to the proximal channel portion between an open position and a closed position. The surgical end effector further comprising a staple cartridge removably seated in the cartridge jaw, wherein the staple cartridge is configured to slide along the longitudinal axis into the proximal channel portion of the cartridge jaw when the distal portion is in the open position.

In another aspect, the present disclosure provides a surgical stapling assembly, comprising a channel. The channel comprising a proximal channel portion extending distally along a longitudinal axis, and a distal channel portion movably coupled to the proximal channel portion. The surgical stapling assembly further comprises a replaceable staple cartridge configured to slide into the proximal channel portion along the longitudinal axis to an installed position in the channel.

In another aspect, the present disclosure provides a method of replacing a staple cartridge in a cartridge jaw of a surgical end effector of a robotic surgical tool. The method comprising moving a distal portion of the cartridge jaw from a closed position to an open position, sliding a first staple cartridge distally out of the cartridge jaw, sliding a second staple cartridge proximally into the cartridge jaw, and moving the distal portion of the cartridge jaw to the closed position to secure the second staple cartridge in the cartridge jaw.

BRIEF DESCRIPTION OF THE FIGURES

The novel features of the various aspects are set forth with particularity in the appended claims. The described aspects, however, both as to organization and methods of operation, may be best understood by reference to the following description, taken in conjunction with the accompanying drawings in which:

Corresponding reference characters indicate corresponding parts throughout the several views. The exemplifications set out herein illustrate various aspects of the present disclosure, in one form, and such exemplifications are not to be construed as limiting the scope of the invention in any manner.

DESCRIPTION

Figure 1:
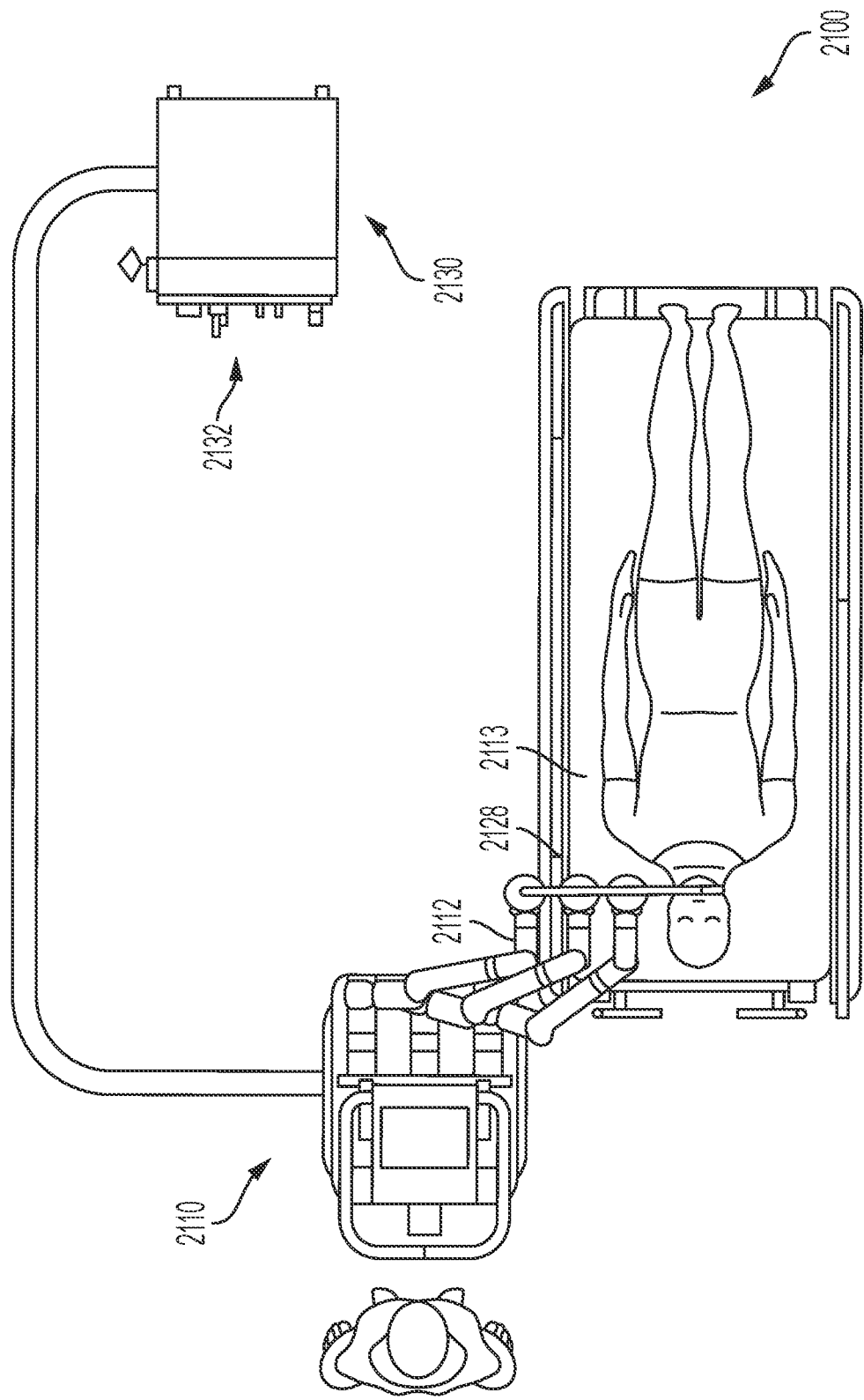
FIG. 1 is a plan view of a surgical procedure depicting a cart-based robotic system arranged for diagnostic and/or therapeutic bronchoscopy procedure(s), in accordance with at least one aspect of the present disclosure.

Applicant of the present application also owns the following U.S. patent applications, filed on Jun. 30, 2021, each of which is herein incorporated by reference in its entirety:

U.S. patent application Ser. No. 17/363,560, titled GRASPING WORK DETERMINATION AND INDICATIONS THEREOF, now U.S. Patent Application Publication No. 2023/0001579;

U.S. patent application Ser. No. 17/363,573, titled LINK-DRIVEN ARTICULATION DEVICE FOR A SURGICAL DEVICE, now U.S. Patent Publication No. 2023/0000578; and U.S. patent application Ser. No. 17/363,578, titled ELECTROSURGICAL TOOL WITH CAPACITIVE COUPLING MITIGATION SHEATH ASSEMBLY, now U.S. Patent Application Publication No. 2023/0000542.

Applicant of the present application also owns the following U.S. patent applications, filed Dec. 30, 2020, each of which is herein incorporated by reference in its entirety:

U.S. patent application Ser. No. 17/137,829, titled SURGICAL TOOL WITH TOOL-BASED TRANSLATION AND LOCK FOR THE SAME;

U.S. patent application Ser. No. 17/137,846, titled ROBOTIC SURGICAL TOOLS HAVING DUAL ARTICULATION DRIVES;

U.S. patent application Ser. No. 17/137,852, titled TORQUE-BASED TRANSITION BETWEEN OPERATING GEARS; and U.S. patent application Ser. No. 17/137,857, titled DUAL DRIVING PINION CROSSCHECK.

Applicant of the present application also owns U.S. patent application Ser. No. 16/587,744, filed Sep. 30, 2019, titled COMMUNICATING CLOSURE EFFORT FOR ROBOTIC SURGICAL TOOLS BACKGROUND, which published Apr. 1, 2021 as U.S. Patent Application Publication No. 2021/0093409, which is incorporated by reference herein in its entirety.

Applicant of the present application also owns U.S. patent application Ser. No. 16/553,725, filed Aug. 28, 2019, titled ARTICULATING INCLUDING ANTAGONISTIC CONTROLS FOR ARTICULATION AND CALIBRATION, which published Mar. 4, 2021 as U.S. Patent Application Publication No. 2021/0059777, which is incorporated by reference herein in its entirety.

Applicant of the present application also owns the following U.S. patent applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS, which issued May 25, 2021 as U.S. Pat. No. 11,013,563;

U.S. patent application Ser. No. 15/940,676, titled AUTOMATIC TOOL ADJUSTMENTS FOR ROBOT-ASSISTED SURGICAL PLATFORMS, which published Jul. 4, 2019 as U.S. Patent Application Publication No. 2019/0201142; and U.S. patent application Ser. No. 15/940,711, titled SENSING ARRANGEMENTS FOR ROBOT-ASSISTED SURGICAL PLATFORMS, which published Jul. 4, 2019 as U.S. Patent Application Publication No. 2019/0201120.

Applicant of the present application also owns U.S. Provisional Patent Application Ser. No. 62/611,339, titled ROBOT ASSISTED SURGICAL PLATFORM, filed Dec. 28, 2017, which is incorporated by reference herein in its entirety.

Application of the present application also owns U.S. patent application Ser. No. 13/118,241, titled SURGICAL STAPLING INSTRUMENTS WITH ROTATABLE STAPLE DEPLOYMENT ARRANGEMENTS, filed May 27, 2011, which issued Jul. 7, 2015 as U.S. Pat. No. 9,072,535, which is incorporated by reference herein in its entirety.

U.S. Pat. No. 10,470,830, titled SYSTEM AND METHODS FOR INSTRUMENT BASED INSERTION ARCHITECTURES, issued Nov. 12, 2019, is also incorporated by reference herein in its entirety.

Before explaining various aspects of a robotic surgical platforms and surgical devices in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Minimally-invasive surgery (MIS), such as laparoscopic surgery and bronchoscopy, typically involves techniques intended to reduce tissue damage during a surgical procedure. For example, laparoscopic procedures can involve creating a number of small incisions in the patient (e.g., in the abdomen) and introducing one or more surgical tools (e.g., end effectors and an endoscope) through the incisions into the patient. Bronchoscopy can involve passing a bronchoscope through a patient's nose and/or mouth, down the patient's throat, and into the patient's lungs. Surgical procedures may then be performed using the introduced surgical tools and with visualization aid provided by the endoscope, for example.

MIS may provide certain benefits, such as reduced patient scarring, less patient pain, shorter patient recovery periods, and/or lower medical treatment costs associated with patient recovery. Recent technological developments allow robotic systems to perform more MIS procedures. The robotic systems typically include one or more robotic arms for manipulating surgical tools based on commands from a remote operator (e.g. surgeon/clinician). A robotic arm may, for example, support at its distal end various surgical devices such as surgical end effectors, imaging devices, and cannulas for providing access to the patient's body cavity and organs.

Existing robotically-assisted surgical systems typically consist of a surgeon console and a patient-side cart with one or more interactive robotic arms controlled from the console. For example, one robotic arm can support a camera and the other robotic arm(s) can support robotic tools such as scalpels, scissors, graspers, and staplers, for example. Various exemplary robotic tools are further described herein.

A robotic surgical system disclosed herein can be a software-controlled, electro-mechanical system designed for clinicians to perform MIS procedures. The robotic surgical system can be used with an endoscope, compatible endoscopic instruments, and accessories. The system may be used by trained clinicians (e.g. physicians/surgeons) in an operating room environment to assist in the accurate control of compatible endoscopic instruments during robotically-assisted urologic, gynecologic, gastrological, and other laparoscopic surgical procedures. The compatible endoscopic instruments and accessories for use with the surgical system are intended for endoscopic manipulation of tissue including stapling, grasping, cutting, blunt and sharp dissection, approximation, ligation, electrocautery, and suturing, for example.

An exemplary robotic system 2100 is shown in FIG. 1, which depicts a cart-based robotically-enabled system arranged for a diagnostic and/or therapeutic bronchoscopy procedure. During a bronchoscopy, the system 2100 may include a cart 2110 having one or more robotic arms 2112 to deliver a surgical device, such as a steerable endoscope 2113, which may be a procedure-specific bronchoscope for bronchoscopy, to a natural orifice access point (i.e., the mouth of the patient positioned on a table in the present example) to deliver diagnostic and/or therapeutic tools. As shown, the cart 2110 may be positioned proximate to the patient's upper torso in order to provide access to the access point. Similarly, the robotic arms 2112 may be actuated to position the bronchoscope relative to the access point. The arrangement in FIG. 1 may also be utilized when performing a gastro-intestinal (GI) procedure with a gastroscope, a specialized endoscope for GI procedures.

With continued reference to FIG. 1, once the cart 2110 is properly positioned, the robotic arms 2112 may insert the steerable endoscope 2113 into the patient robotically, manually, or a combination thereof. The endoscope 2113 may be directed down the patient's trachea and lungs after insertion using precise commands from the robotic system until reaching the target destination or operative site. For example, the endoscope 2113 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 2113 may endoscopically deliver tools to resect the potentially cancerous tissue. In some instances, diagnostic and therapeutic treatments can be delivered in separate procedures. In those circumstances, the endoscope 2113 may also be used to deliver a fiducial to "mark" the location of the target nodule as well. In other instances, diagnostic and therapeutic treatments may be delivered during the same procedure.

The system 2100 may also include a movable tower 2130, which may be connected via support cables to the cart 2110 to provide support for controls, electronics, fluidics, optics, sensors, and/or power to the cart 2110. Placing such functionality in the tower 2130 allows for a smaller form factor cart 2110 that may be more easily adjusted and/or re-positioned by an operating clinician (e.g. surgeon) and his/her staff. Additionally, the division of functionality between the cart/table and the tower 2130 reduces operating room clutter and facilitates improving clinical workflow. While the cart 2110 may be positioned close to the patient, the tower 2130 may be stowed in a remote location to stay out of the way during a procedure.

In support of the robotic systems described above, the tower 2130 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 2130 or the cart 2110, may control the entire system or sub-system(s) thereof. For example, when executed by a processor of the computer system, the instructions may cause the components of the robotics system to actuate the relevant carriages and arm mounts, actuate the robotics arms, and control the robotic surgical tools. For example, in response to receiving the control signal, the motors in the joints of the robotics arms may position the arms into a certain posture.

The tower 2130 may also include a pump, flow meter, valve control, and/or fluid access in order to provide controlled irrigation and aspiration capabilities to the system that may be deployed through the endoscope 2113. These components may also be controlled using the computer system of tower 2130. In some aspects, irrigation and aspiration capabilities may be delivered directly to the endoscope 2113 through separate cable(s).

The tower 2130 may include a voltage and surge protector designed to provide filtered and protected electrical power to the cart 2110, thereby avoiding placement of a power transformer and other auxiliary power components in the cart 2110, resulting in a smaller, more moveable cart 2110.

The tower 2130 may also include support equipment for the sensors deployed throughout the robotic system 2100. For example, the tower 2130 may include opto-electronics equipment for detecting, receiving, and processing data received from the optical sensors or cameras throughout the robotic system 2100. In combination with the control system, such opto-electronics equipment may be used to generate real-time images for display in any number of consoles deployed throughout the system, including in the tower 2130. Similarly, the tower 2130 may also include an electronic subsystem for receiving and processing signals received from deployed electromagnetic (EM) sensors. The tower 2130 may also be used to house and position an EM field generator for detection by EM sensors in or on the robotic surgical tool. The tower 2130 can also house an electrosurgical generator for supplying RF current to a robotic surgical tool, such as monopolar scissors, for example.

The tower 2130 may also include a console 2132 in addition to other consoles available in the rest of the system, e.g., a console mounted on top of the cart 2110. The console 2132 may include a user interface and a display screen, such as a touchscreen, for the clinician. Consoles in the system 2100 are generally designed to provide both robotic controls as well as pre-operative and real-time information of the procedure, such as navigational and localization information of the endoscope 2113. When the console 2132 is not the only console available to the clinician, it may be used by a second clinician, such as a nurse, for example, to monitor the health or vitals of the patient and the operation of system, as well as provide procedure-specific data, such as navigational and localization information. In other aspects, the console 2132 is housed in a body that is separate from the tower 2130.

The tower 2130 may be coupled to the cart 2110 and endoscope 2113 through one or more cables or connections. In some aspects, the support functionality from the tower 2130 may be provided through a single cable to the cart 2110, simplifying and de-cluttering the operating room. In other aspects, specific functionality may be coupled in separate cabling and connections. For example, while power may be provided through a single power cable to the cart, the support for controls, optics, fluidics, and/or navigation may be provided through one or more separate cables.

Figure 2:
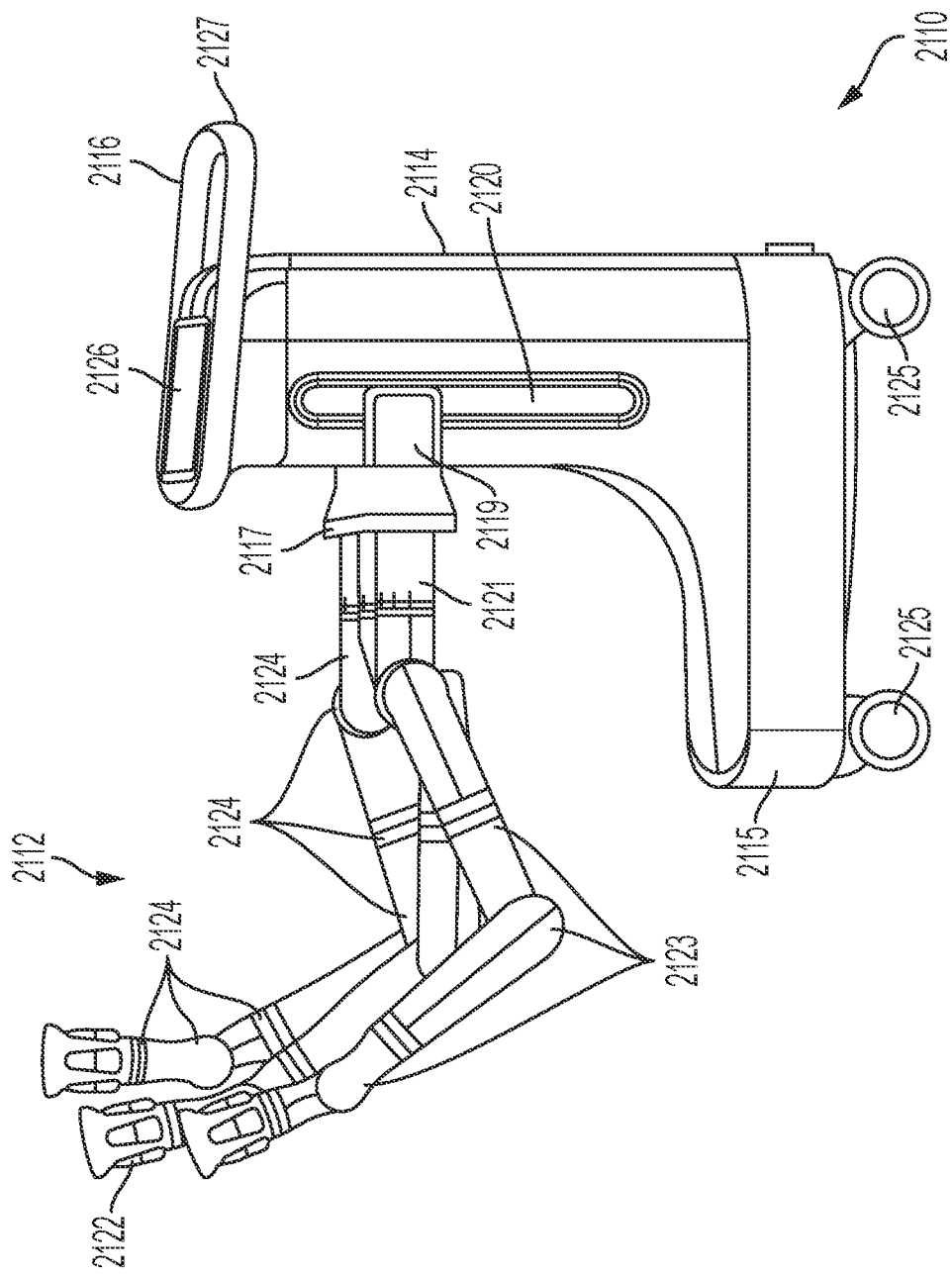
FIG. 2 is a perspective view of a robotic arm cart of the cart-based robotic system of FIG. 1, in accordance with at least one aspect of the present disclosure.

FIG. 2 depicts the cart 2110 from the cart-based robotically-enabled system 2100 shown in FIG. 1. The cart 2110 generally includes an elongated support structure 2114 (often referred to as a "column"), a cart base 2115, and a console 2116 at the top of the elongated support structure

2114. The elongated support structure 2114 may include one or more carriages, such as a carriage 2117 (alternatively "arm support") for supporting the deployment of one or more robotic arms 2112 (three shown in FIG. 2). The carriage 2117 may include individually configurable arm mounts that rotate along a perpendicular axis to adjust the base of the robotic arms 2112 for better positioning relative to the patient. The carriage 2117 also includes a carriage interface 2119 that allows the carriage 2117 to vertically translate along the elongated support structure 2114.

The carriage interface 2119 is connected to the elongated support structure 2114 through slots, such as slot 2120, that are positioned on opposite sides of the elongated support structure 2114 to guide the vertical translation of the carriage 2117. The slot 2120 contains a vertical translation interface to position and hold the carriage at various vertical heights relative to the cart base 2115. Vertical translation of the carriage 2117 allows the cart 2110 to adjust the reach of the robotic arms 2112 to meet a variety of table heights, patient sizes, and physician preferences. Similarly, the individually configurable arm mounts on the carriage 2117 allow the robotic arm base 2121 of robotic arms 2112 to be angled in a variety of configurations.

The elongated support structure 2114 may include internal mechanisms, such as gears and motors, that are designed to use a vertically aligned lead screw to translate the carriage 2117 in a mechanized fashion in response to control signals generated in response to user inputs, e.g., inputs from the console 2116.

The robotic arms 2112 may generally include robotic arm bases 2121 and tool drivers 2122, separated by a series of linkages 2123 that are connected by a series of joints 2124, each joint including an independent actuator, each actuator including an independently controllable motor. Each independently controllable joint represents an independent degree of freedom available to the robotic arm. Each of the arms 2112 have seven joints, and thus provide seven degrees of freedom. A multitude of joints result in a multitude of degrees of freedom, allowing for "redundant" degrees of freedom. Redundant degrees of freedom allow the robotic arms 2112 to position their respective tool drivers 2122 at a specific position, orientation, and trajectory in space using different linkage positions and joint angles. This allows for the system to position and direct a robotic surgical tool from a desired point in space while allowing the clinician to move the arm joints into a clinically advantageous position away from the patient to create greater access while avoiding arm collisions.

The cart base 2115 balances the weight of the elongated support structure 2114, carriage 2117, and arms 2112 over the floor. Accordingly, the cart base 2115 houses heavier components, such as electronics, motors, power supply, as well as components that either enable movement and/or immobilize the cart. For example, the cart base 2115 includes rollable wheel-shaped casters 2125 that allow for the cart 2110 to easily move around the room prior to a procedure. After reaching the appropriate position, the casters 2125 may be immobilized using wheel locks to hold the cart 2110 in place during the procedure.

Positioned at a vertical end of elongated support structure 2114, the console 2116 allows for both a user interface for receiving user input and a display screen (or a dual-purpose device such as, for example, a touchscreen 2126) to provide the clinician with both pre-operative and intra-operative data. Potential pre-operative data on the touchscreen 2126 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 2116 may be positioned and tilted to allow a clinician to access the console from the side of the elongated support structure 2114 opposite carriage 2117. From this position, the clinician may view the console 2116, robotic arms 2112, and patient while operating the console 2116 from behind the cart 2110. As shown, the console 2116 also includes a handle 2127 to assist with maneuvering and stabilizing cart 2110.

The distal end of the system's robotic arms include the tool driver 2122 (alternatively referred to as "instrument drive mechanism" or "instrument device manipulator" (IDM)) that incorporate electro-mechanical means for actuating the robotic tool. A removable or detachable robotic tool can be releasably mounted to the tool driver 2122. The robotic tool can be devoid of any electro-mechanical components, such as motors. This dichotomy may be driven by the need to sterilize robotic surgical tools used in medical procedures, and the inability to adequately sterilize expensive capital equipment due to their intricate mechanical assemblies and sensitive electronics. Accordingly, the robotic surgical tools may be designed to be detached, removed, and interchanged from the instrument driver (and thus the system) for individual sterilization or disposal by the clinician or the clinician's staff. In contrast, the instrument drivers need not be changed or sterilized, and may be draped for protection.

Figure 3:
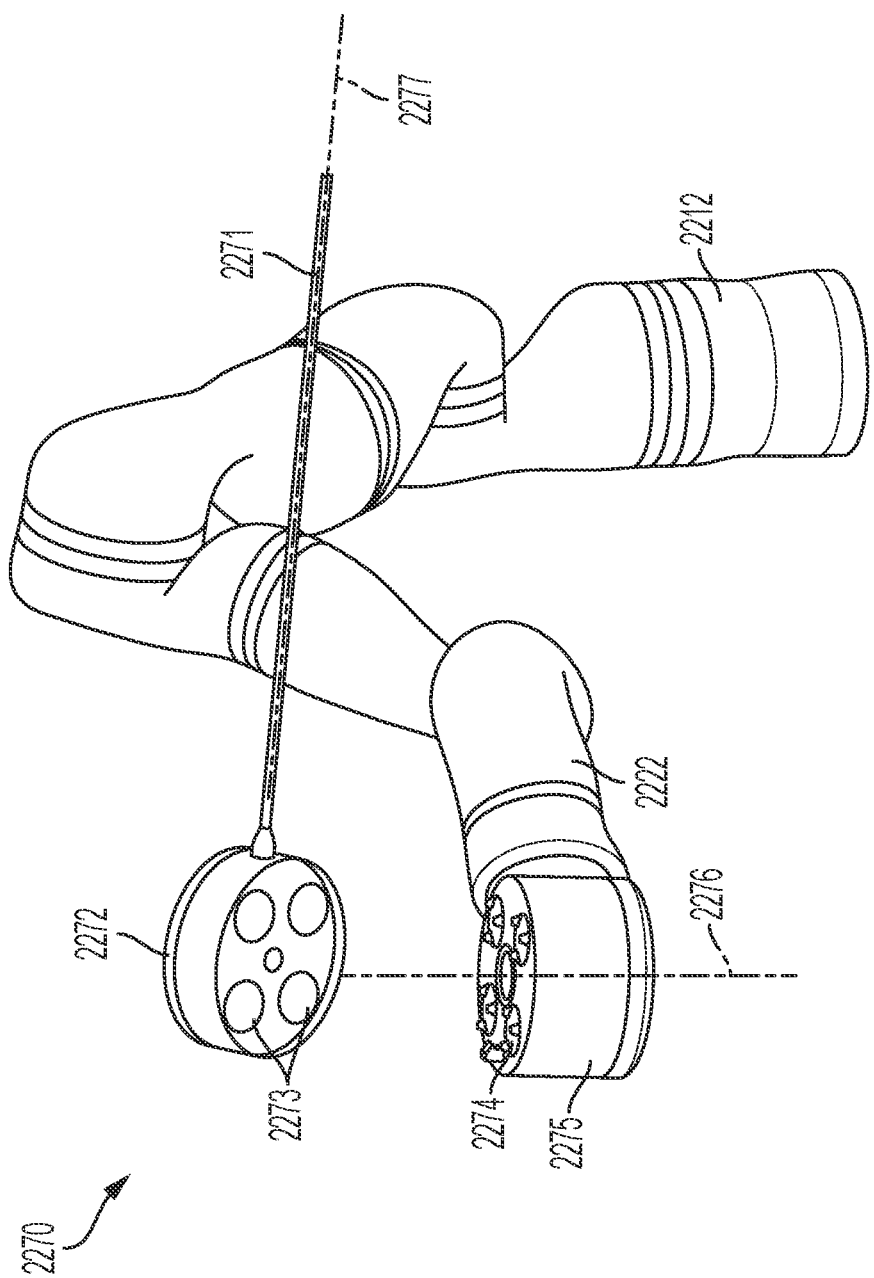
FIG. 3 is a perspective view of a robotic arm having a tool driver and a paired robotic tool detached from the tool driver, in accordance with at least one aspect of the present disclosure.
Figure 4:
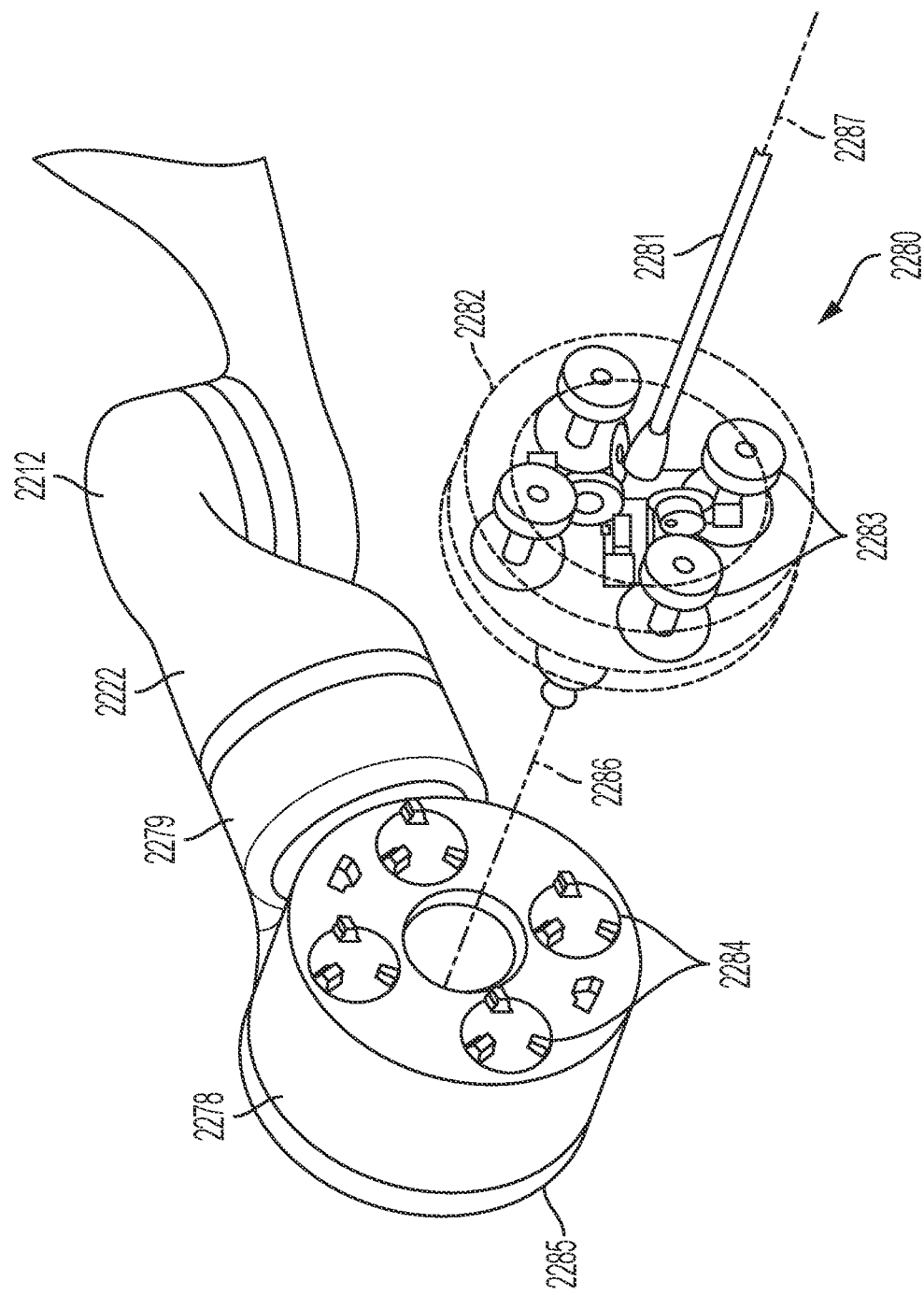
FIG. 4 is another perspective view of the robotic arm of FIG. 3 having a tool driver and a paired robotic tool detached from the tool driver, in accordance with at least one aspect of the present disclosure.

FIGS. 3 and 4 illustrate an example tool driver paired with a robotic surgical tool. The tool drivers are positioned at the distal end 2222 of a robotic arm 2212, which can be similar in many aspects to the robotic arms 2112. Positioned at the distal end 2222 of the robotic arm 2212, the tool drivers comprises one or more drive units arranged with parallel axes to provide controlled torque to a robotic surgical tool via drive shafts. Each drive unit includes an individual drive shaft for interacting with the instrument, a gear head for converting the motor shaft rotation to a desired torque, a motor for generating the drive torque, an encoder to measure the speed of the motor shaft and provide feedback to the control circuitry, and control circuitry for receiving control signals and actuating the drive unit. Each drive unit being independently controlled and motorized, the tool driver may provide multiple (four as shown in FIGS. 3 and 4) independent drive outputs to the robotic surgical tool. In operation, the control circuitry can receive a control signal, transmit a motor signal to the motor, compare the resulting motor speed as measured by the encoder with the desired speed, and modulate the motor signal to generate the desired torque, for example.

For procedures that require a sterile environment, the robotic system may incorporate a drive interface, such as a sterile adapter connected to a sterile drape, that sits between the tool driver and the robotic surgical tool. The chief purpose of the sterile adapter is to transfer angular motion from the drive shafts of the tool driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the tool driver and drive inputs on the instrument. Connected to the sterile adapter, the sterile drape, comprised of a thin, flexible material such as transparent or translucent plastic, is designed to cover the capital equipment, such as the tool driver, the robotic arm, and the cart (in a cart-based system) or table (in a table-based system). Use of the drape would allow the capital equipment to be positioned proximate to the patient while still being located in an area not requiring sterilization (i.e., non-sterile field). On the other side of the sterile drape, the robotic surgical tool may interface with the patient in an area requiring sterilization (i.e., sterile field).

Robotic surgical platforms like the robotic surgical system 2100 are further described in U.S. Patent Application Publication No. 2021/0059777, titled ARTICULATING INCLUDING ANTAGONISTIC CONTROLS FOR ARTICULATION AND CALIBRATION, published Mar. 4, 2021. U.S. Patent Application Publication No. 2021/0059777, titled ARTICULATING INCLUDING ANTAGONISTIC CONTROLS FOR ARTICULATION AND CALIBRATION, published Mar. 4, 2021 is incorporated by reference herein in its entirety.

FIG. 3 depicts a robotic surgical tool 2270 with a paired tool driver 2275. The tool driver 2275 can be coupled to a distal end 2222 of the robotic arm 2212. Like other surgical tools designed for use with a robotic system, the robotic surgical tool 2270 includes an elongated shaft 2271 (or elongate body) and a housing (or base) 2272. The housing 2272, can also be referred to as an "instrument handle" due to its intended design for manual interaction by the clinician when attaching or coupling the surgical tool 2270 to the tool driver 2275 on the robotic arm 2212. The housing 2272 includes rotatable drive inputs 2273, e.g., receptacles, pulleys or spools, that are designed to be mated with drive outputs 2274 that extend through a drive interface on tool driver 2275 at the distal end 2222 of the robotic arm 2212. When physically connected, latched, and/or coupled, the mated drive inputs 2273 of housing 2272 may share axes of rotation with the drive outputs 2274 in the tool driver 2275 to allow the transfer of torque from drive outputs 2274 to drive inputs 2273. In some instances, the drive outputs 2274 may include splines that are designed to mate with receptacles on the drive inputs 2273. The drive outputs 2274 (and drive inputs 2273 when drivingly coupled thereto) are configured to rotate about axes parallel with a central axis 2276 defined through the tool driver 2275.

The elongated shaft 2271 is designed to be delivered through either an anatomical opening or lumen, e.g., as in endoscopy, or a minimally invasive incision, e.g., as in laparoscopy. The elongated shaft 2271 may be either flexible (e.g., having properties similar to an endoscope) or rigid (e.g., having properties similar to a laparoscope) or contain a customized combination of both flexible and rigid portions. In an unflexed configuration, the elongated shaft 2271 extends along a longitudinal axis 2277, which is transverse to the central axis 2276 of the tool driver 2275. When designed for laparoscopy, the distal end of a rigid elongated shaft may be connected to an end effector extending from a jointed wrist formed from a clevis with at least one degree of freedom and a surgical tool or robotic surgical tool, such as, for example, a grasper, scissors, a stapler, or other surgical device. The end effector can be actuated based on force from the tendons as the drive inputs 2273 rotate in response to torque received from the drive outputs 2274 of the tool driver 2275. Various highly articulatable robotic surgical tools are further described herein. When designed for endoscopy, the distal end of a flexible elongated shaft may include a steerable or controllable bending section that may be articulated and bent based on torque received from the drive outputs 2274 of the tool driver 2275.

Torque from the tool driver 2275 is transmitted down the elongated shaft 2271 using tendons along the shaft 2271. These individual tendons, such as pull wires, may be individually anchored to individual drive inputs 2273 within the housing 2272. From the housing 2272, the tendons are directed down one or more pull lumens along the elongated shaft 2271 and anchored at the distal portion of the elongated shaft 2271 or in the wrist at the distal portion of the elongated shaft 2271. During a surgical procedure, such as a laparoscopic, endoscopic or hybrid procedure, these tendons may be coupled to a distally mounted end effector, such as a grasper or scissors, for example. Under such an arrangement, torque exerted on drive inputs 2273 would transfer tension to the tendon, thereby causing the end effector to actuate in some way. In some instances, during a surgical procedure, the tendon may cause a joint to rotate about an axis, thereby causing the end effector to move in one direction or another. Alternatively, the tendon may be connected to one or more jaws of a grasper at distal end of the elongated shaft 2271, where tension from the tendon cause the grasper to close.

In endoscopy, the tendons may be coupled to a bending or articulating section positioned along the elongated shaft 2271 (e.g., at the distal end) via adhesive, a control ring, or other mechanical fixation. When fixedly attached to the distal end of a bending section, torque exerted on drive inputs 2273 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 2271 to allow for controlled articulation in the desired bending or articulable sections.

In endoscopy, the elongated shaft 2271 houses a number of components to assist with the robotic procedure. The shaft may include a working channel for deploying surgical tools (or robotic surgical tools), irrigation, and/or aspiration to the operative region at the distal end of the shaft 2271. The shaft 2271 may also accommodate wires and/or optical fibers to transfer signals to/from an optical assembly at the distal tip, which may include an optical camera. The shaft 2271 may also accommodate optical fibers to carry light from proximally-located light sources, such as light emitting diodes, to the distal end of the shaft. In various instances, an RF electrode can extend through the elongated shaft 2271 and can be configured to deliver RF energy to a distal end effector of the robotic surgical tool 2270.

At the distal end of the robotic surgical tool 2270, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

Referring still to FIG. 3, the drive shaft axes, and thus the drive input axes, are parallel to the central axis 2276 of the tool driver 2275 and orthogonal to the longitudinal axis 2277 of the elongated shaft. This arrangement, however, can complicate roll capabilities for the elongated shaft 2271 in certain instances. Rolling the elongated shaft 2271 along its longitudinal axis 2277 while keeping the drive inputs 2273 static may result in undesirable tangling of the tendons as they extend off the drive inputs 2273 and enter pull lumens within the elongated shaft 2271. The resulting entanglement of such tendons may disrupt any control algorithms intended to predict movement of the flexible elongated shaft during an endoscopic procedure.

FIG. 4 illustrates another tool driver 2285 and a paired robotic surgical tool 2280 where the axes of the drive units are parallel to an axis defined by an elongated shaft 2281 of the surgical tool 2280. As shown, a circular tool driver 2285 comprises four drive units with their drive outputs 2284 aligned in parallel at the end of the robotic arm 2212. The drive units, and their respective drive outputs 2284, are housed in a rotational assembly 2278 of the tool driver 2285 that is driven by one of the drive units within the rotational assembly 2278. In response to torque provided by the rotational drive unit, the rotational assembly 2278 rotates along a circular bearing that connects the rotational assembly 2278 to a non-rotational portion 2279 of the tool driver 2285. Power and controls signals may be communicated from the non-rotational portion 2279 of the tool driver 2285 to the rotational assembly 2278 through electrical contacts, which can be maintained through rotation by a brushed slip ring connection. In other aspects of the present disclosure, the rotational assembly 2278 may be responsive to a separate drive unit that is integrated into the non-rotational portion 2279, and thus not in parallel to the other drive units. The rotational assembly 2278 allows the tool driver 2285 to rotate the drive units, and their respective drive outputs 2284, as a single unit around a tool driver axis 2286.

Similar to the robotic surgical tool 2270, the robotic surgical tool 2280 includes an elongated shaft portion 2281 and a housing 2282 (shown as transparent in FIG. 4 for illustrative purposes) including a plurality of drive inputs 2283 (such as receptacles, pulleys, and spools) that are configured to receive the drive outputs 2284 in the tool driver 2285. Shaft 2281 extends from the center of the housing 2282 along a longitudinal axis 2287 substantially parallel to the axes of the drive inputs 2283, rather than orthogonal thereto as in the arrangement shown in FIG. 3.

When coupled to the rotational assembly 2278 of the tool driver 2285, the robotic surgical tool 2280, comprising the housing 2282 and shaft 2281, rotates in combination with the rotational assembly 2278 about a central axis 2286 defined through the tool driver 2285. Since the shaft 2281 is positioned at the center of the housing 2282, the shaft 2281 is coaxial with tool driver's central axis 2286 when attached. Thus, rotation of the rotational assembly 2278 causes the shaft 2281 to rotate about its own longitudinal axis 2287. Moreover, as the rotational assembly 2278 rotates with the shaft 2281, any tendons connected to the drive inputs 2283 in the housing 2282 are not tangled during rotation. Accordingly, the parallelism of the axes of the drive outputs 2284, drive inputs 2283, and shaft 2281 allows for the shaft rotation without tangling any control tendons.

In other instances, the tool drives may include a different configuration of actuated drives. For example, U.S. Patent Application Publication No. 2019/0201111, titled DRIVE ARRANGEMENTS FOR ROBOTIC-ASSISTED SURGICAL PLATFORMS, which published on Jul. 4, 2019, describes tool carriages having various drive arrangements. U.S. Pat. No. 9,072,535, titled SURGICAL STAPLING INSTRUMENTS WITH ROTATABLE STAPLE DEPLOYMENT ARRANGEMENTS, which issued Jul. 7, 2015, also describes tool carriages having various drive arrangements. U.S. Pat. No. 9,072,535, titled SURGICAL STAPLING INSTRUMENTS WITH ROTATABLE STAPLE DEPLOYMENT ARRANGEMENTS, which issued Jul. 7, 2015, and U.S. Patent Application Publication No. 2019/0201111, titled DRIVE ARRANGEMENTS FOR ROBOTIC-ASSISTED SURGICAL PLATFORMS, which published on Jul. 4, 2019, are incorporated by reference herein in their respective entireties. Alternative drive arrangements are further described herein.

Figure 5:
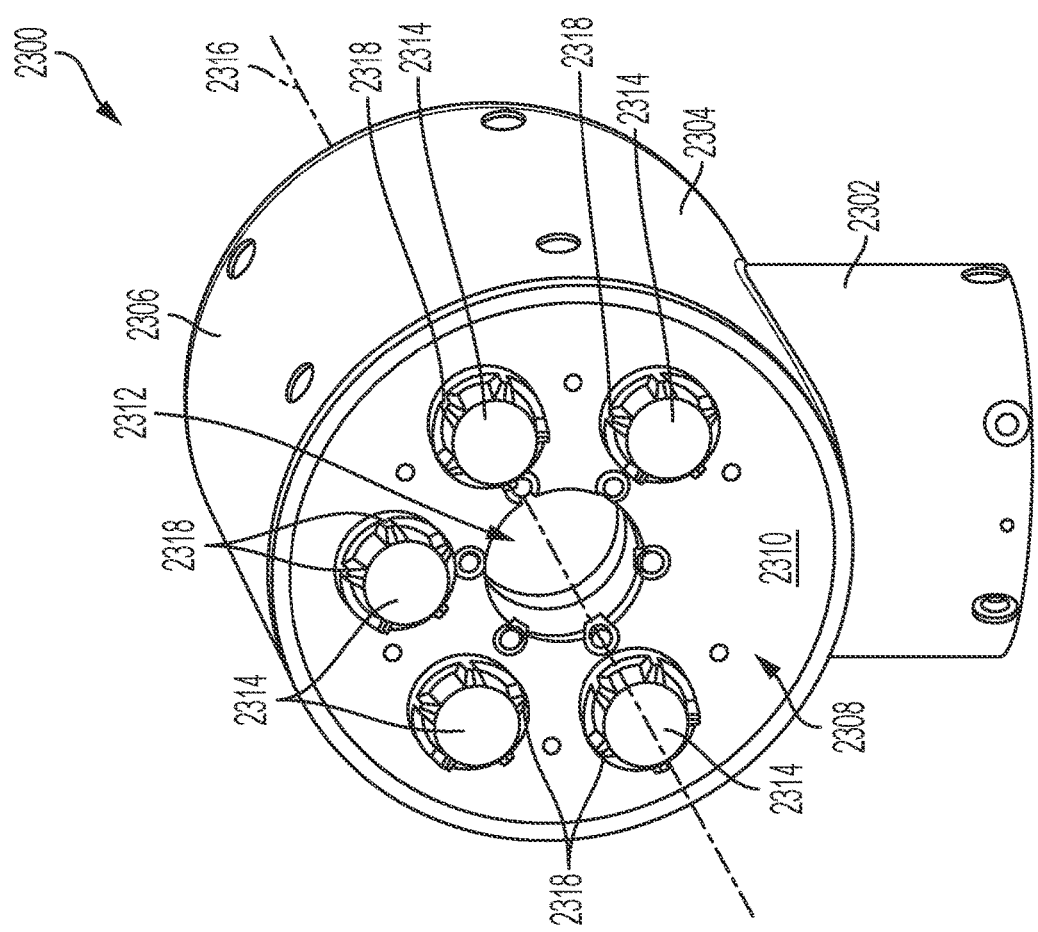
FIG. 5 is a perspective view of a tool driver, in accordance with at least one aspect of the present disclosure.

FIG. 5 depicts a perspective view of another tool driver 2300, which is also referred to herein as an IDM. The tool driver 2300 is similar in many aspects to the tool drivers 2285; however, the tool driver 2300 includes five rotary outputs. Various aspects of the tool driver 2300 are further described in U.S. Pat. No. 10,470,830, titled SYSTEM AND METHODS FOR INSTRUMENT BASED INSERTION ARCHITECTURES, issued Nov. 12, 2019, for example.

The tool driver 2300 can be used with the robotic surgical system 2100 and with the robotic arms 2212, for example. The tool driver 2300 is configured to attach a surgical tool to a robotic arm in a manner that allows the surgical tool to be continuously rotated, or "rolled", about a longitudinal axis of the surgical tool. The tool driver 2300 includes a base 2302 and a surgical tool holder assembly 2304 coupled to the base 2302. The surgical tool holder assembly 2304 serves as a tool holder for holding a robotic surgical tool.

Figure 6:
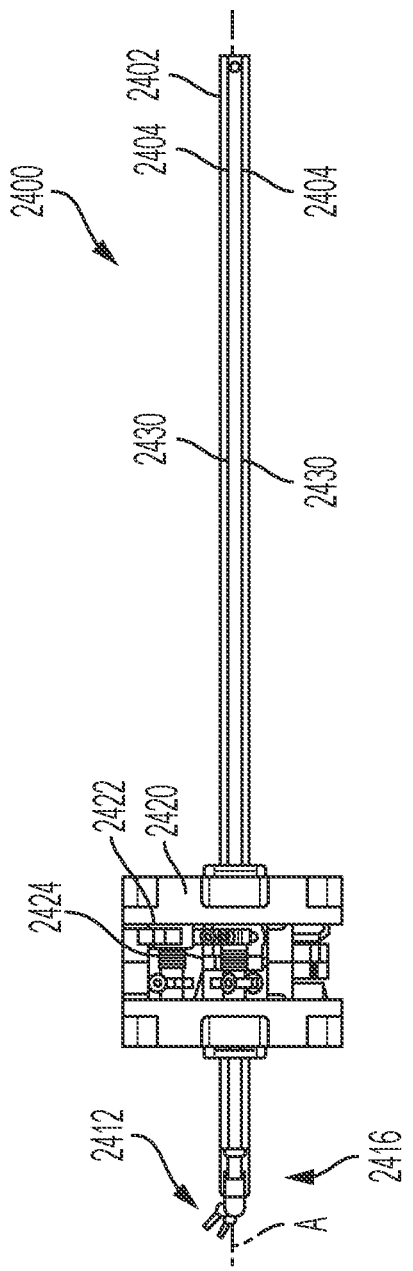
FIG. 6 is an elevation view of a surgical tool for use with the tool driver of FIG. 5, in accordance with at least one aspect of the present disclosure.

The surgical tool holder assembly 2304 further includes an outer housing 2306, a surgical tool holder 2308, an attachment interface 2310, a passage 2312, and a plurality of torque couplers 2314 that have splines 2318. The passage 2312 comprises a through-bore that extends from one face of the tool driver 2300 to an opposing face of the tool driver 2300 along a central axis 2316, which is collinear with a longitudinal axis of the surgical tool coupled thereto. The tool driver 2300 can be used with a variety of surgical tools, which may include a handle, or housing, and an elongated body, or shaft, and which may be for a laparoscope, an endoscope, or other types of surgical tools, such as electrosurgical tools including monopolar RF scissors, for example. An exemplary surgical tool 2400 is shown in FIG. 6, for example.

The base 2302 removably or fixedly mounts the tool driver 2300 to a robotic surgical arm of a robotic surgical system. In FIG. 5, the base 2302 is fixedly attached to the outer housing 2306 of the surgical tool holder assembly 2304. In alternative instances, the base 2302 is structured to include a platform, which is adapted to rotatably receive the surgical tool holder 2308 on the face opposite from the attachment interface 2310. The platform may include a passage aligned with the passage 2312 to receive the elongated body of the surgical tool and, in some instances, an additional elongated body of a second surgical tool mounted coaxially with the first surgical tool. One or more motors can be housed in the base 2302. For example, the surgical tool holder 2308 can include multiple motors, which are configured to drive, i.e. rotate output drives, also referred to herein as torque drivers and torque couplers, 2314 with a torque and rotary velocity, which can be controlled by the controller, for example.

The surgical tool holder assembly 2304 is configured to secure a surgical tool to the tool driver 2300 and rotate the surgical tool relative to the base 2302. Mechanical and electrical connections are provided from the surgical arm to the base 2302 and then to the surgical tool holder assembly 2304 to rotate the surgical tool holder 2308 relative to the outer housing 2306 and to manipulate and/or deliver power and/or signals from the surgical arm to the surgical tool holder 2308 and ultimately to the surgical tool. Signals may include signals for pneumatic pressure, electrical power, electrical signals, and/or optical signals.

The attachment interface 2310 is a face of the surgical tool holder 2308 that attaches to the surgical tool. The attachment interface 2310 includes a first portion of an attachment mechanism that reciprocally mates with a second portion of the attachment mechanism located on the surgical tool. The attachment interface 2310 is further described in U.S. Pat. No. 10,470,830, titled SYSTEM AND METHODS FOR INSTRUMENT BASED INSERTION ARCHITECTURES, issued Nov. 12, 2019, for example.

Various tools can attach to the tool driver 2300, including tools used for laparoscopic, endoscopic and endoluminal surgery. Tools can include tool-based insertion architectures that reduce the reliance on robotic arms for insertion. In other words, insertion of a surgical tool (e.g., towards a surgical site) can be facilitated by the design and architecture of the surgical tool. For example, in some instances, wherein a tool comprises an elongated shaft and a handle, the architecture of the tool enables the elongated shaft to translate longitudinally relative to the handle along an axis of insertion. Various advantages of tool-based insertion architectures are further described in U.S. Pat. No. 10,470,830, titled SYSTEM AND METHODS FOR INSTRUMENT BASED INSERTION ARCHITECTURES, issued Nov. 12, 2019, which is incorporated by reference herein its entirety.

A surgical tool 2400 having a tool-based insertion architecture is shown in FIG. 6. Various aspects of the surgical tool 2400 are further described in U.S. Pat. No. 10,470,830, titled SYSTEM AND METHODS FOR INSTRUMENT BASED INSERTION ARCHITECTURES, issued Nov. 12, 2019, for example.

The surgical tool 2400 enables a translation of the surgical tool 2400 (e.g., translation of its shaft 2402 and end effector 2412 relative to a tool driver and/or distal end of the robotic arm) along an insertion axis. In such instances, the surgical tool 2400 can be moved along the insertion axis without reliance—or with less reliance—on movement of a robotic arm. The surgical tool 2400 includes an elongated shaft 2402, an end effector 2412 connected to the shaft 2402, and a handle 2420, which may also be referred to as an instrument housing or base, coupled to the shaft 2402. The elongated shaft 2402 comprises a tubular member and includes one or more channels or grooves 2404 along its outer surface. The grooves 2404 are configured to receive one or more wires or cables 2430 therethrough. The cables 2430 run along an outer surface of the elongated shaft 2402. In other aspects of the present disclosure, certain cables 2430 can run through the shaft 2402 and may not be exposed. Manipulation of the cables 2430 (e.g., via the tool driver 2300) results in actuation of the end effector 2412, for example.

The end effector 2412 can include laparoscopic, endoscopic, or endoluminal components, for example, and can be designed to provide an effect to a surgical site. For example, the end effector 2412 can comprise a wrist, grasper, tines, forceps, scissors, clamp, knife, and/or fasteners. Exemplary surgical end effectors are further described herein. The cables 2430 that extend along the grooves on the outer surface of the shaft 2402 can actuate the end effector 2412. The cables 2430 extend from a proximal portion of the shaft 2402, through the handle 2420, and toward a distal portion of the shaft 2402, where they actuate the end effector 2412.

The instrument housing 2420 includes an attachment interface 2422 having one or more mechanical inputs 2424, e.g., receptacles, pulleys or spools, that are designed to be reciprocally mated with one or more torque couplers 2314 (FIG. 5) on the attachment interface 2310 of the tool driver 2300. The attachment interface 2422 is capable of attaching to the tool driver 2300 via a front-mount, back-mount and/or top mount. When physically connected, latched, and/or coupled together, the mated mechanical inputs 2424 of the instrument handle 2420 may share axes of rotation with the torque couplers 2314 of the tool driver 2300, thereby allowing the transfer of torque from the motors in the tool driver 2300 to the instrument handle 2420. In some instances, the torque couplers 2314 may comprise splines that are designed to mate with receptacles on the mechanical inputs. Cables 2430 that actuate the end effector 2412 engage the receptacles, pulleys, or spools of the handle 2420, such that the transfer of torque from the tool driver 2300 to the instrument handle 2420 results in actuation of the end effector 2412.

The surgical tool 2400 can include a first actuation mechanism that controls actuation of the end effector 2412. The surgical tool 2400 can also include a second actuation mechanism that enables the shaft 2402 to translate relative to the handle 2420 along an axis of insertion A. One or more additional actuation mechanism can effect articulation of the end effector 2412 relative to the shaft 2402. For example, the surgical tool 2400 can include an articulation joint 2416, which can allow articulation of the end effector 2412 relative to the shaft 2402 about one or more axes.

In various instances, an actuation mechanism can include one or more pulleys mounted on a rotary axis to change relative cable length and, in other instances, mounting a pulley on a lever, gear or track-based system to adjust its location. Additionally or alternatively, ball spline rotary shafts that travel down a length of a tool can also be used to transmit forces in a mechanically-remote way. Various actuation mechanisms are further described in U.S. Pat. No. 10,470,830, titled SYSTEM AND METHODS FOR INSTRUMENT BASED INSERTION ARCHITECTURES, issued Nov. 12, 2019, for example.

In various instances, the surgical tool 2400 can be a surgical stapler, disposable loading unit, or stapling assembly for cutting and stapling tissue. The surgical stapler can integrally include or be adapted to receive one or more staple cartridges (e.g. a replaceable staple cartridge) therein. A staple cartridge can include multiple longitudinal rows of staple cavities and a longitudinal knife slot, in certain instances. Staples are contained within the staple cavities and are configured to be sequentially fired during a firing stroke (e.g. a proximal-to-distal firing stroke) of a firing member (e.g. an E-beam or I-beam) through the staple cartridge. In various instances, a rotary drive shaft can transmit the firing forces to the firing member. For example, rotation of the rotary drive shaft in the end effector can move the firing member during the firing stroke to engage a sled, staple drivers, and/or staple drivers and to drive the staples into tissue.

In certain instances, a replaceable staple cartridge can be removed from a surgical stapler and replaced with a new or fresh staple cartridge before initiating a subsequent stapling motion. For example, the end effector 2412 can be structured and dimensioned to receive a removable staple cartridge therein. Removal and installation of a replaceable staple cartridge is often completed at the surgical site by a clinician, such as surgeon and/or nurse assisting in the surgical procedure. In various instances, it can require a large amount of force applied in a particular direction to remove the staple cartridge from the cartridge jaw. For example, a clinician may knock or push a bottom surface of the cartridge jaw against a surface (e.g. a table or hand) in the operating room to release the replaceable staple cartridge installed therein. The force can disengage engagement features between the replaceable staple cartridge and the cartridge jaw, which can allow the replaceable staple cartridge to pivot out of the cartridge jaw.

Figure 7A:
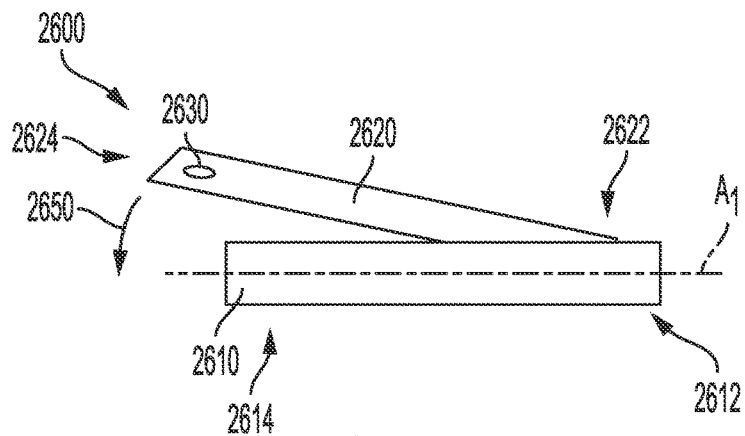
FIGS. 7A and 7B are schematics depicting a staple cartridge being installed into a cartridge jaw (FIG. 7A) and being uninstalled from the cartridge jaw (FIG. 7B), according to at least one aspect of the present disclosure.

FIG. 7A is a schematic of a surgical stapling assembly 2600 including a staple cartridge 2620 and a cartridge jaw 2610. The staple cartridge 2620 can include multiple rows of deployable fasteners (e.g. staples), which can be sequentially lifted from within the cartridge body and driven into tissue to form a seal, for example. The force to install the staple cartridge 2620 may be applied in a direction 2650. The staple cartridge 2620 is installed by first placing a proximal end 2622 of the staple cartridge 2620 into a proximal end 2612 of an elongate channel defined in the cartridge jaw 2610. The force may be applied to the distal end 2624 of the staple cartridge 2620 in the direction 2650 to pivot the distal end 2624 of the staple cartridge 2620 counterclockwise and downward into the distal end 2614 of the cartridge jaw 2610. The staple cartridge 2620 is fully seated or installed in the cartridge jaw 2610 when pan bumps 2630 along each lateral side of the staple cartridge 2620 snap into recesses in the cartridge jaw 2610. When fully seated, the staple cartridge 2620 is parallel or substantially parallel to the cartridge jaw 2610 and a longitudinal axis A1.

Figure 7B:
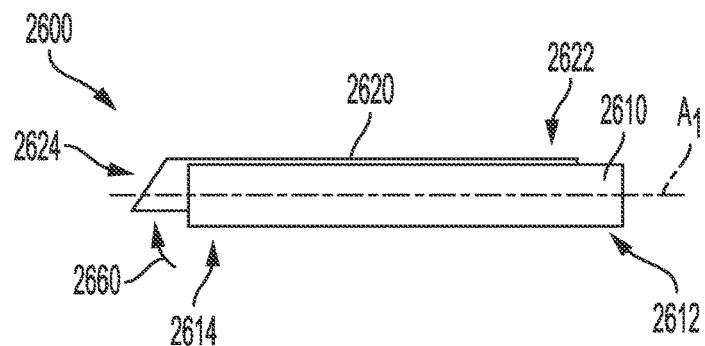

FIG. 7B is another schematic of the surgical stapling assembly 2600 depicting the staple cartridge 2620 installed in the cartridge jaw 2610 and a removal force for uninstalling the staple cartridge 2620 being applied at the distal end 2624 of the staple cartridge 2620 in a direction 2660. The removal force is applied to the distal end 2624 while the cartridge jaw 2610 is held stationary. The removal force can move the distal end 2624 of the staple cartridge 2620 upwards in the direction 2660 and may then pivot the distal end 2624 clockwise and upwards vertically away from the distal end 2614 of the cartridge jaw 2610. As the distal end 2624 moves away from the cartridge jaw 2610, the pan bumps 2630 may snap out of the recesses in the cartridge jaw 2610 allowing the staple cartridge 2620 to be removed from the cartridge jaw 2610. Once the staple cartridge 2620 is removed, a new staple cartridge may be installed into the cartridge jaw 2610 as shown in FIG. 7A.

In some instances, it can be difficult to apply the requisite amount of force at the appropriate angle to remove the staple cartridge from the cartridge jaw. For example, a robotic tool may have too much slack in the joints and/or mechanisms thereof to apply the requisite force. More specifically, when the robotic tool is unattached from the surgical robot and/or when the joints and mechanisms thereof are otherwise unlocked, the robotic tool can be too floppy to sufficiently knock against a surface to release a replaceable staple cartridge therein. As a result, without locking the joints of the stapling device, the joints may be able to move freely, which can hinder a user's ability to apply the necessary force in the correct way to remove the replaceable staple cartridge.

In certain instances, the removal force can be applied at roughly a ninety-degree angle to the cartridge jaw (i.e. perpendicular to a longitudinal axis of the replaceable staple cartridge and/or cartridge jaw and through a tissue-facing or tissue-supporting surface thereof). For example, a significant removal force may be required to snap certain cartridge detent features, such as pan bumps on the lateral sides thereof, for example, over the cartridge jaw retention features, such as channel recesses in the lateral sides thereof, for example. Moreover, the cartridge jaw tends to be a small component making it hard to hold the cartridge jaw stationary when applying the necessary force to remove the replaceable staple cartridge. In certain instances, locking the joints of the robotic tool can hold the cartridge jaw stationary; however, to lock the joints, the surgical tool may be required to be installed on a robotic arm, which can be cumbersome for the clinician in certain instances. Additionally, even when attached to a robotic arm, free movement of the joints and mechanisms in the robotic tool may be preferred in certain instances to ensure drive motions are not transferred to the robotic tool during the installation/uninstallation of the staple cartridge.

In certain instances, a staple cartridge can be uninstalled longitudinally, rather than pivoting out of engagement with the cartridge jaw. When uninstalled longitudinally, the staple cartridge can be removed along a longitudinal axis of the staple cartridge and/or cartridge jaw. For example, a distal retaining feature on the cartridge jaw can be removed to open the cartridge jaw, which can provide a clearance or pathway for the staple cartridge to slide in/out of the cartridge jaw. In such instances, a reduced amount of force may be required to release the staple cartridge from the cartridge jaw. Longitudinal removal of the staple cartridge can be utilized in robotic surgical tools such that the staple cartridge can be removed from the robotic surgical tool even when the robotically-controlled joints and mechanisms are unlocked or slack. Such a staple cartridge can also be removed from a non-robotic surgical tool, such as the end effector of a handheld surgical stapler, for example. In such instances, replaceable staple cartridges for handheld stapling instruments and robotic surgical tools can be identical and fungible. For example, a replaceable staple cartridge for a handheld stapling instrument can be interchangeable or swappable with a replaceable staple cartridge for a robotic surgical tool.

In one aspect of the present disclosure, a cartridge jaw can have a movable retaining feature in the distal portion thereof. In an open or unlocked position, the movable retaining feature can allow a staple cartridge to slide longitudinally into a seated position in the cartridge jaw and to slide longitudinally out of the seated position from the cartridge jaw. The movable retaining features can lock into place when the staple cartridge is fully seated in the cartridge jaw to prevent premature removal of the staple cartridge. For example, the movable retaining feature can be a distal portion of the cartridge jaw that is releasably locked to a proximal portion of the cartridge jaw.

Figure 8A:
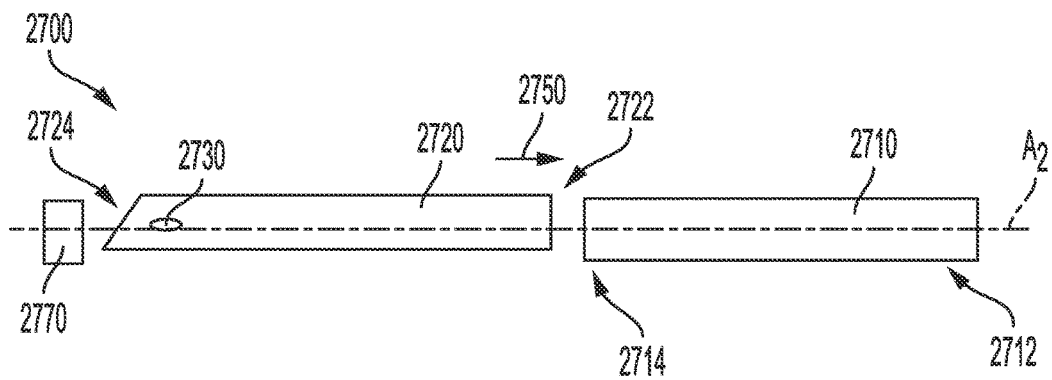
FIGS. 8A and 8B are schematics depicting a staple cartridge being installed into a cartridge jaw (FIG. 8A) and being uninstalled from the cartridge jaw (FIG. 8B), according to at least one aspect of the present disclosure.
Figure 8B:
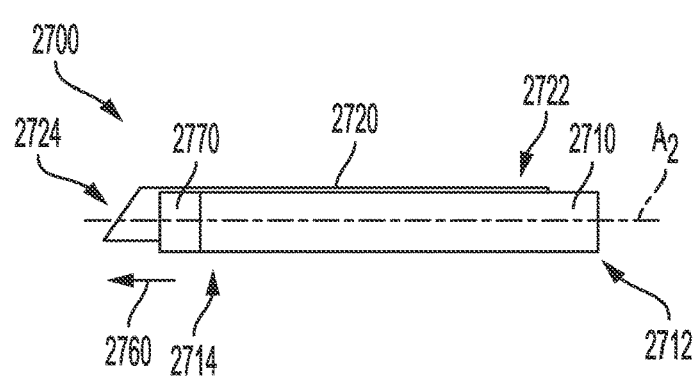

FIG. 8A is a schematic of a surgical stapling assembly 2700 having a cartridge jaw design that allows a staple cartridge 2720 to be installed into a cartridge jaw 2710 along a longitudinal axis $A_2$. The staple cartridge 2720 may be substantially similar to the staple cartridge 2620. A first step of installing the staple cartridge 2720 into the cartridge jaw 2710 involves opening or releasing a distal portion 2770 of the cartridge jaw 2710. In FIG. 8A, the distal portion 2770 is detached from the cartridge jaw 2710. The proximal end 2722 of the staple cartridge 2720 can then slide into a proximal portion 2712 of the cartridge jaw 2710 in a proximal direction 2750 along the longitudinal axis $A_2$. The staple cartridge 2720 may be inserted longitudinally into an elongate channel in the cartridge jaw 2710. As the staple cartridge 2720 slides into the elongate channel, a bottom exterior surface of the staple cartridge 2720 rests against a bottom interior surface of the elongate channel. The staple cartridge 2720 slides into the cartridge jaw 2710 until it is fully inserted. The pan bumps 2730 on the staple cartridge 2720 may rest inside of recesses in the elongate channel when the staple cartridge 2720 is fully inserted. Upon fully seating the staple cartridge 2720 in the cartridge jaw 2710, the distal portion 2770 may be attached to a distal end 2714 of the proximal portion 2712 of the cartridge jaw 2710 to lock the staple cartridge 2720 in place. FIG. 8B shows the staple cartridge 2720 installed into the cartridge jaw 2710. In other instances, the distal end 2724 of the staple cartridge 2720 can be seated within the distal portion 2770 such that the staple cartridge 2720 does not protrude distally out of the cartridge jaw 2710 upon fully seating the staple cartridge 2720 in the cartridge jaw 2710.

To remove the staple cartridge 2720 from the cartridge jaw 2710, the distal portion 2770 may be detached and moved in a distal direction 2760. Once the distal portion is detached, the distal end 2724 of the staple cartridge 2720 can be pulled longitudinally in the distal direction 2760 to remove the staple cartridge 2720 from the cartridge jaw 2710. Then the steps described above in regards to FIG. 8A can be repeated to install a new staple cartridge 2720.

In certain instances, the cartridge jaw channel may include a channel cutout that is configured to receive a lug of the staple cartridge. The moveable distal portion of the cartridge jaw may be used to open the channel cutout, which can allow the staple cartridge to slide into or out of position on the proximal piece of the channel. In some instances, the staple cartridge overcomes a friction fit to slide into position on the proximal piece of the channel. Reattaching the distal portion of the channel, upon installation of the staple cartridge, can allow the staple cartridge to be locked in place longitudinally within the cartridge jaw. Various mechanisms can be used to lock the distal retaining feature(s) (e.g. distal channel portion(s)) to the cartridge jaw, including friction or snap-fit features and/or springs, for example.

In such instances, the force to install and uninstall a replaceable staple cartridge may be reduced in certain instances. Additionally or alternatively, the replaceable staple cartridge can be installed or uninstalled without needing to stiffen any joints, e.g. an articulation joint, of a surgical tool. The cartridge jaw design could be used in a robotic stapling tool or in a handheld stapling instrument and, in both instances, may reduce the requisite force for installing and/or uninstalling the replaceable staple cartridge.

Figure 9:
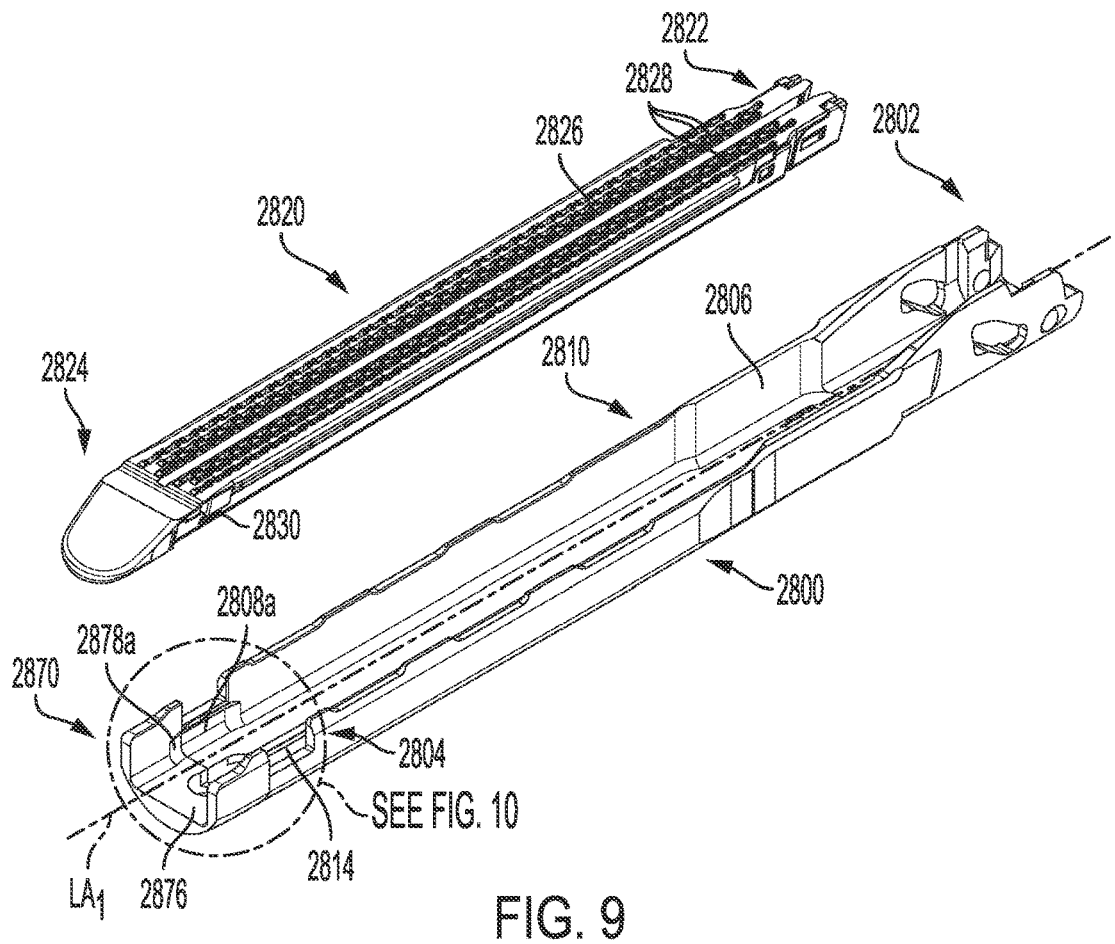
FIG. 9 is a perspective view a cartridge jaw with an attached distal portion in a closed position and a staple cartridge ready to be installed in the cartridge jaw, according to at least one aspect of the present disclosure.

FIGS. 9-14 depict a cartridge jaw 2800 that is configured to slidably receive a staple cartridge 2820 therein longitudinally along a longitudinal axis $LA_1$ defined by the cartridge jaw 2800. In FIG. 9, the staple cartridge 2820 is outside (e.g. uninstalled from) the cartridge jaw 2800. In various instances, an end effector (e.g. the end effector 2412 in FIG. 6) may be a surgical cutting and fastening assembly including the cartridge jaw 2800, which is configured to operably support the staple cartridge 2820 therein. For example, the end effector may include a set of jaws with one of them being the cartridge jaw 2800 having the staple cartridge 2820 installable therein with the method described above with respect to FIG. 8A in certain instances.

The staple cartridge 2820 may be similar in many aspects to the staple cartridges 2620 and 2720. In various instances, they are identical and fungible staple cartridges. The staple cartridge 2820 may comprise a proximal end 2822, a distal end 2824, and multiple longitudinal rows of staple cavities 2828, wherein the staples contained within the staple cavities are configured to be sequentially fired during a firing stroke (e.g. a proximal-to-distal firing stroke) of a firing member through the staple cartridge.

Still referring to FIG. 9, the cartridge jaw 2800 includes a separable proximal channel portion 2810 and a distal portion 2870. Separation of the distal portion 2870 from the proximal channel portion 2810 corresponds to opening of the cartridge jaw 2800 to receive a staple cartridge, as further described herein. The proximal channel portion 2810 includes a proximal end 2802, a distal end 2804, and an elongate channel 2806. The cartridge jaw 2800 defines the longitudinal axis $LA_1$ extending along a central axis of the cartridge jaw 2800. A slot 2814 extends along a portion of the proximal channel portion 2810, and a slot 2816 extends along a portion of the distal portion 2870. The slot 2816 can terminate at a distal through-hole through the distal portion 2870. The slots 2814, 2816 are aligned when the distal portion 2870 is mated with the proximal channel portion 2810 to correspond to a closed position of the cartridge jaw 2800. The proximal channel portion 2810 and the distal portion 2870 can be rigid components, which are configured to support a staple cartridge during a firing stroke. For example, the proximal channel portion 2810 and the distal portion 2870 can form a rigid and inflexible assembly when connected together.

When the staple cartridge 2820 is installed within the cartridge jaw 2800, a slot 2826 defined through the cartridge body of the staple cartridge 2820 can be aligned with the slots 2814 and 2816. In use, a firing member (e.g. an I-beam or E-beam) can slide through the aligned slots 2814, 2816, 2826. For example, a bottom foot of the firing beam can engage a groove running along the bottom surface of proximal channel portion 2810 along the length of slot 2814 and into the slot 2816.

Figure 10:
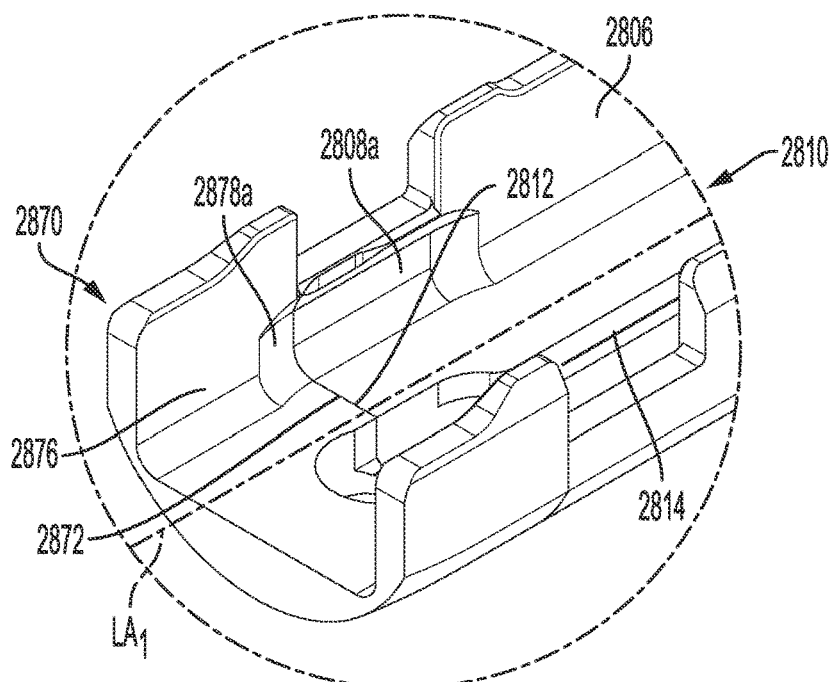
FIG. 10 is a detailed view of the distal portion of the cartridge jaw of FIG. 9 with the distal portion in the closed position, according to at least one aspect of the present disclosure.
Figure 11:
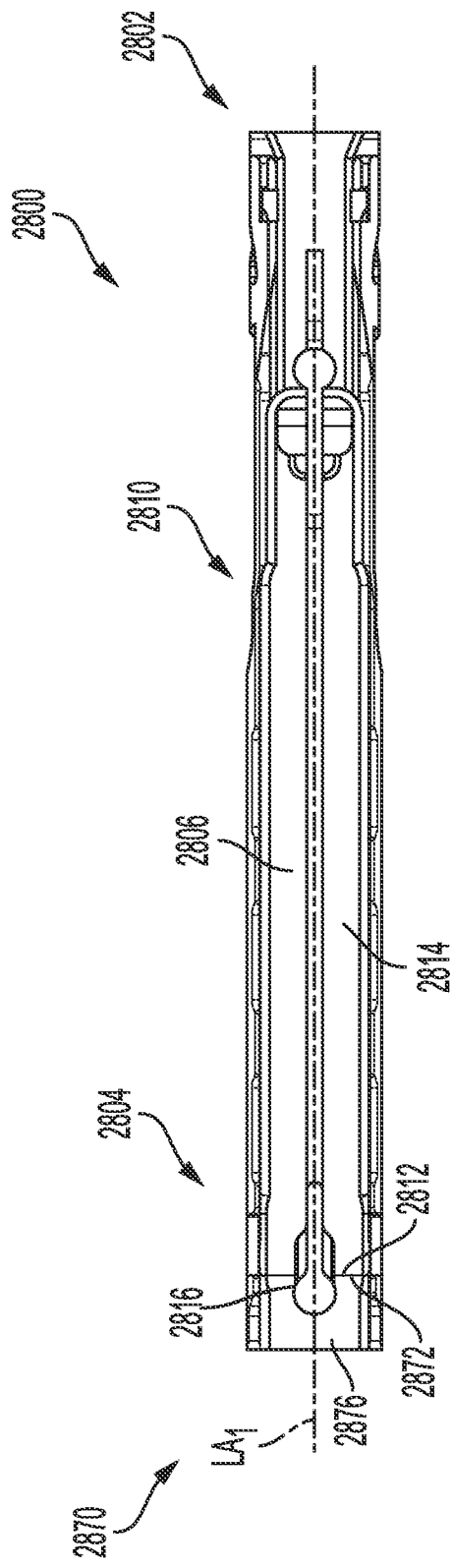
FIG. 11 is a plan view of the cartridge jaw of FIG. 9, according to at least one aspect of the present disclosure.

The cartridge jaw 2800 is shown in the closed position in FIGS. 9-12, which can also be referred to as a locked or engaged position in certain instances. In the closed position, the distal portion 2870 is attached to the distal end 2804 of the proximal channel portion 2810. FIG. 10 shows a detailed view of the distal end portion of the cartridge jaw 2800 in the closed position. When the distal portion 2870 is in the closed position, a distal face 2812 of the proximal channel portion 2810 may be mated against a proximal face 2872 of the distal portion 2870. The channel 2876 of the distal portion 2870 matches the elongate channel 2806 of the proximal channel portion 2810 creating the full elongate channel of the cartridge jaw 2800. In various instances, the distal portion 2870 may complete lug-receiving recesses 2808a, 2808b, when the cartridge jaw 2800 is in the closed position. The lug-receiving recesses 2808a, 2808b may be located on both sides of the proximal channel portion 2810 at the distal end 2804. Lug-receiving recesses 2878a, 2878b of the distal portion 2870 may match with the lug-receiving recesses 2808a, 2808b of the proximal channel portion 2810 forming complete lug-receiving recesses for the detents or pan bumps 2830 on the staple cartridge. When the staple cartridge 2820 is seated in the cartridge jaw 2800, the pan bumps 2830 rest inside of the completed recesses formed by the lug-receiving recesses 2808a, 2808b, 2878a, and 2878b.

The distal portion 2870 may be attachable to the distal end 2804 of the proximal channel portion 2810 in any manner that allows the distal portion 2870 to selectively move from an open position to a closed position. In various instances, snap features may be used to attach the distal portion 2870 to the distal end 2804 of the cartridge jaw 2800 and hold the distal portion 2870 in the closed position. In some instances, the distal portion 2870 can be pivotably attached to the cartridge jaw 2800, and, in certain instances, a torsion spring may be used to hold the distal portion 2870 in the closed position. In some instances, at least one snap feature and at least one torsion spring can be used in combination to hold the distal portion 2870 in the closed position relative to the proximal channel portion 2810.

Figure 12:
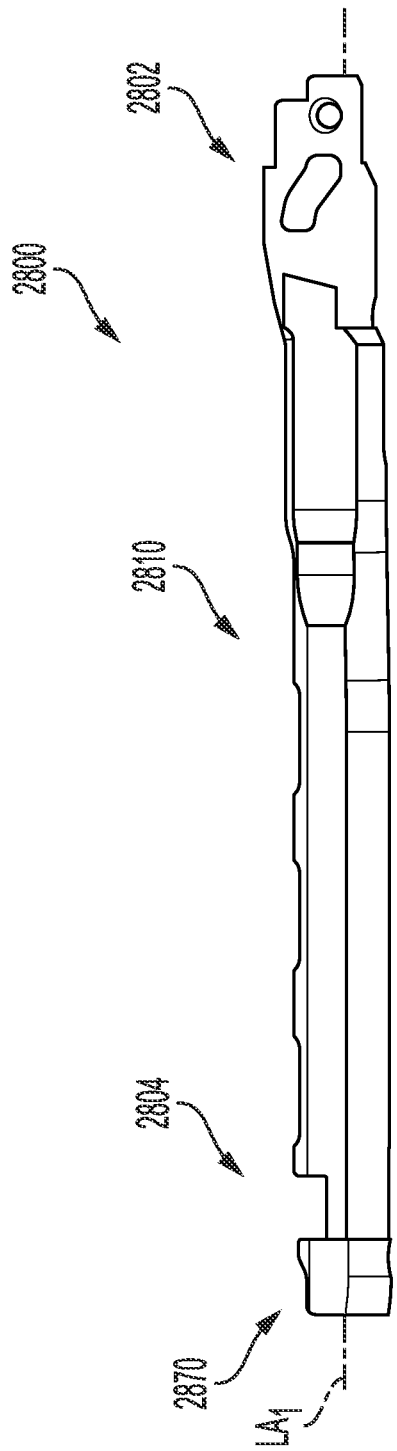
FIG. 12 is an elevation view of the cartridge jaw of FIG. 9, according to at least one aspect of the present disclosure.

FIG. 12 depicts a side view of the cartridge jaw 2800 in the closed position. In some instances, there may be internal snap features that could be used to hold the distal portion in the closed position. Additionally or alternatively, there could be external snap features.

Figure 13:
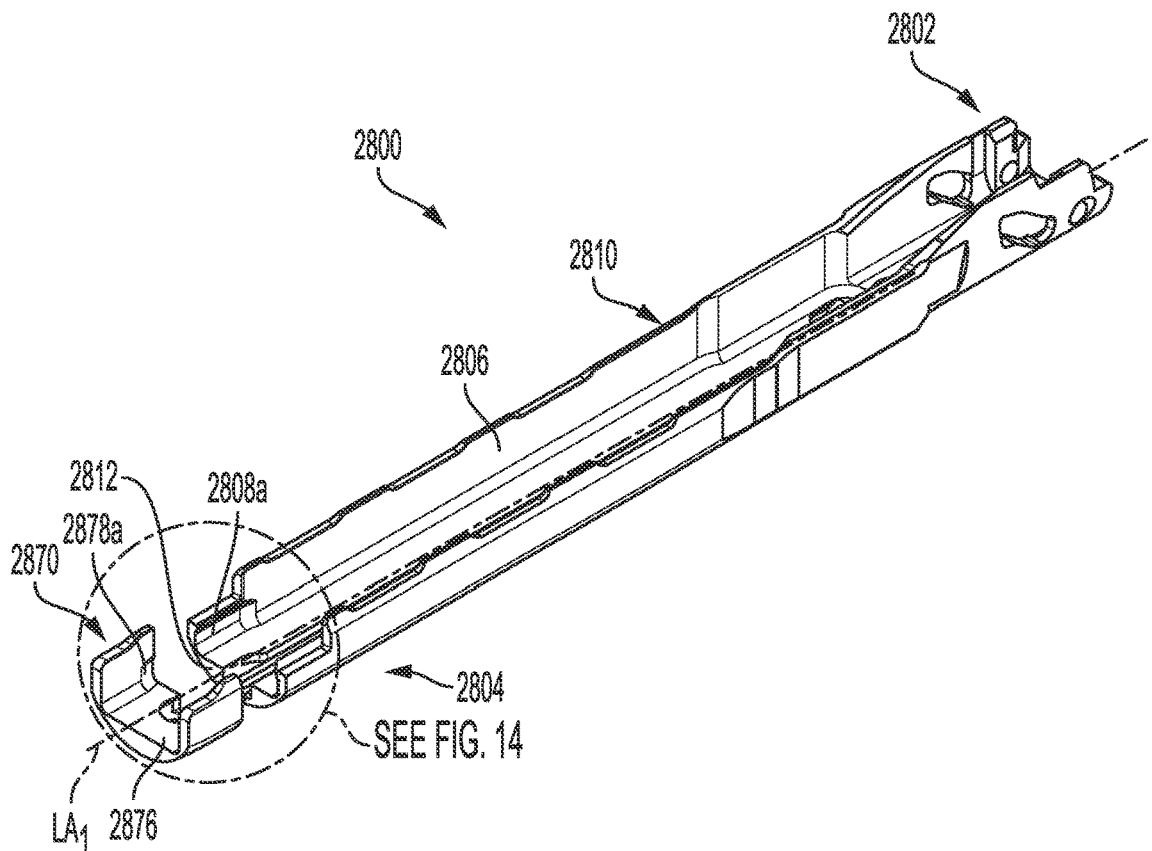
FIG. 13 is a perspective view of the cartridge jaw of FIG. 9 with the distal portion in an open position, according to at least one aspect of the present disclosure.
Figure 14:
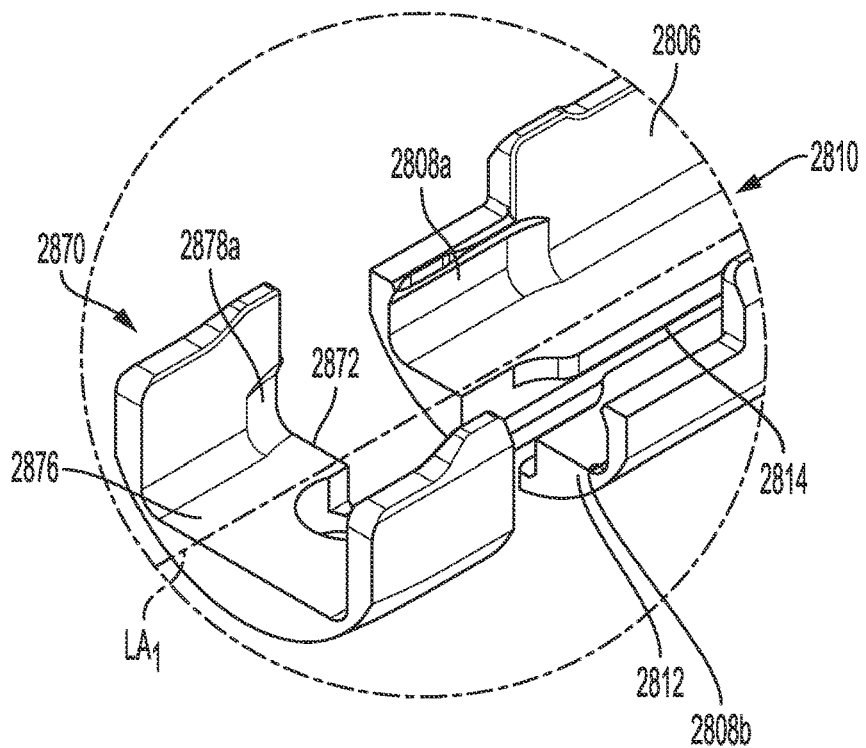
FIG. 14 is a detailed view of the distal portion of the cartridge jaw of FIG. 13 with the distal portion in the open position, according to at least one aspect of the present disclosure.

FIGS. 13 and 14 show the cartridge jaw 2800 in an open position, which could also be referred to as a disengaged or unlocked position. In the open position, the cartridge jaw 2800 may have the staple cartridge 2820 installed therein and/or removed along the longitudinal axis $LA_1$. The staple cartridge 2820 may be installed into the cartridge jaw in the same manner as described in regards to FIG. 8A. For example, after the distal portion 2870 is released to configure the cartridge jaw 2800 in the open position, the staple cartridge 2820 may be slid into the proximal channel portion 2810 along the longitudinal axis $LA_1$. To fully install the staple cartridge 2820, the distal portion 2870 is moved to the closed position in which the distal portion 2870 is placed against the distal end 2804 of the proximal channel portion 2810 to contain the staple cartridge 2820. The pan bumps 2830 rest in of the lug-receiving recesses 2878a, 2878b of the distal portion 2870 and in the lug-receiving recesses 2808a, 2808b of the proximal channel portion 2810. In the closed position, the staple cartridge 2820 can be securely seated in the cartridge jaw 2800 and only removable upon removing the distal portion 2870 to allow the staple cartridge 2820 to be removed longitudinally.

The cartridge jaw 2800 can be moved between the closed position and the open position in a variety of ways. Moving the distal portion 2870 out of the way, allows the staple cartridge 2820 to be installed and uninstalled longitudinally. Referring primarily to FIGS. 13 and 14, the distal portion 2870 is fully removed from the proximal channel portion 2810 and later can be reattached to the proximal channel portion 2810. FIG. 14 shows a detailed view of the distal portion 2870 fully removed from the proximal channel portion 2810. Snap features may be used to detach and reattach the distal portion 2870 to the proximal channel portion 2810.

Figure 15:
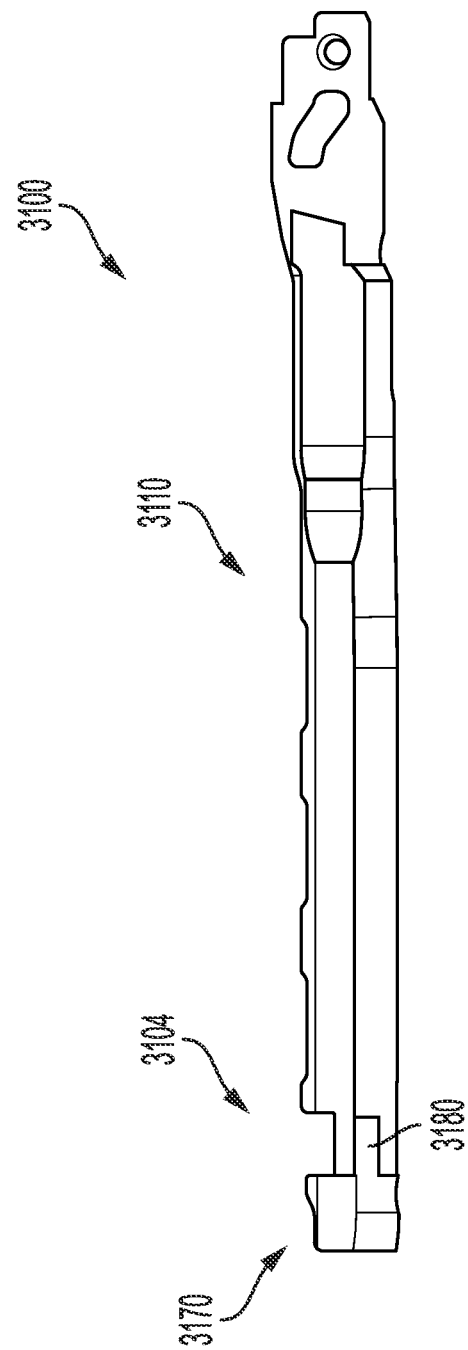
FIG. 15 is an elevation view of a cartridge jaw with distal snap features for releasably connecting a distal portion of the cartridge jaw to a proximal portion of the cartridge jaw, according to at least one aspect of the present disclosure.

Referring now to FIG. 15, a cartridge jaw 3100 is shown. The cartridge jaw 3100 is similar in many aspects to the cartridge jaw 2800; however, the cartridge jaw 3100 includes external side snap features 3180, which are configured to hold a distal portion 3170 against a distal end 3104 of a proximal channel portion 3110. In some instances, the snap feature(s) 3180 may extend over the proximal channel portion 3110 as shown in FIG. 13 and snap into recesses defined into the lateral sidewalls of the proximal channel portion 3110.

Figure 16:
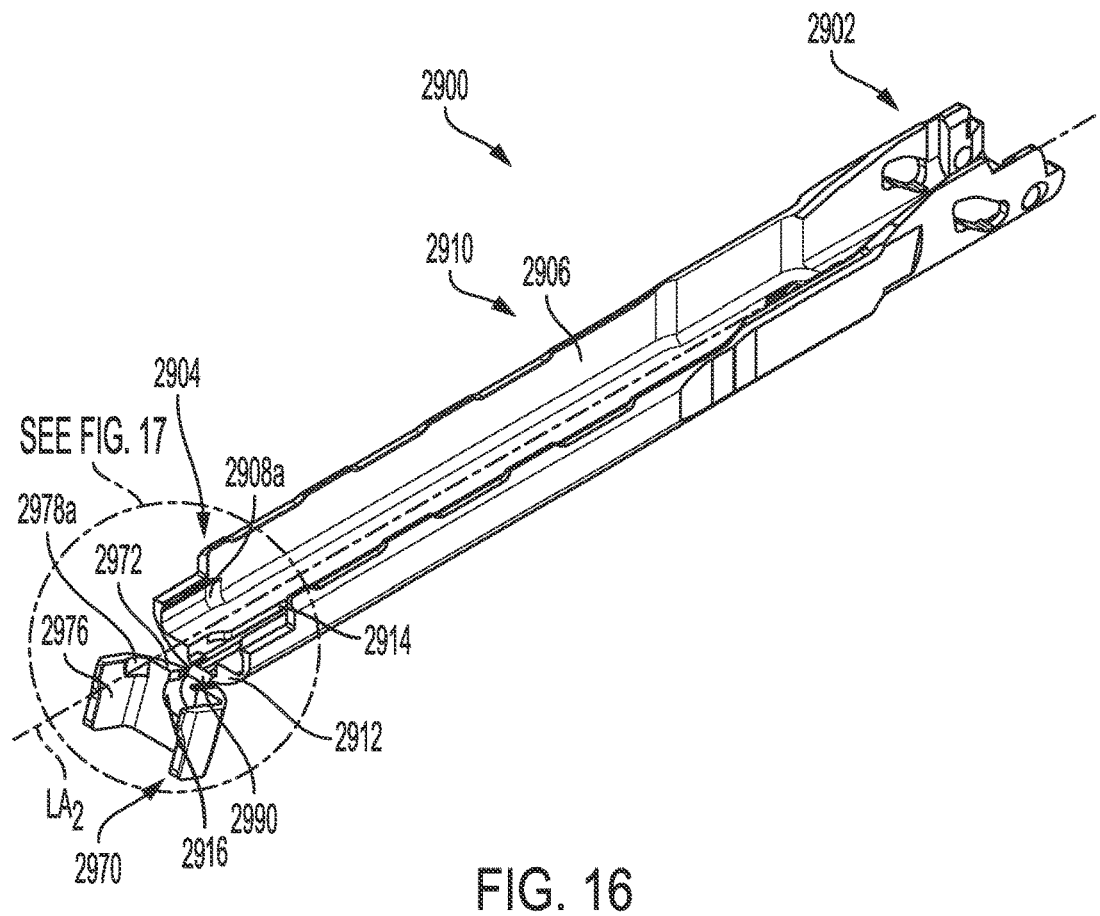
FIG. 16 is a perspective view of a cartridge jaw with a distal portion of the cartridge jaw in an open position and attached to a proximal portion of the cartridge jaw with a torsion spring, according to at least one aspect of the present disclosure.
Figure 17:
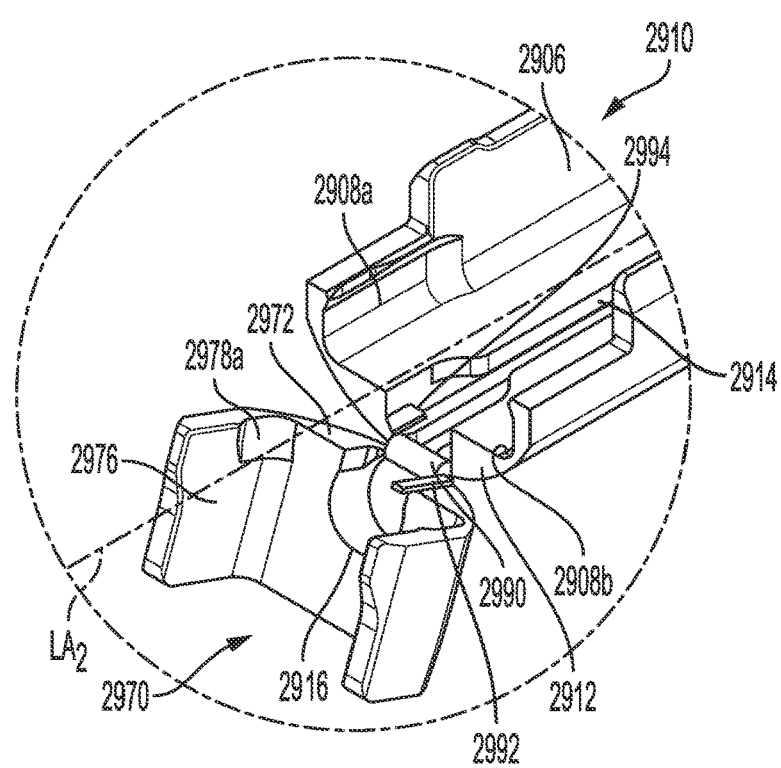
FIG. 17 is a detailed view of the distal portion of the cartridge jaw of FIG. 16 with the distal portion in the open position, according to at least one aspect of the present disclosure.

In some instances, referring now to FIGS. 16 and 17, a distal portion of a channel jaw can be pivotably attached to a proximal channel portion. A pivot between the distal portion and the proximal channel portion can ensure that the distal portion remains attached and is not misplaced during installation or removal of the staple cartridge, for example.

The cartridge jaw 2900 is similar in many aspects to the cartridge jaw 2800; various differences are further described herein. The cartridge jaw 2800 includes a proximal channel portion 2910 and a distal portion 2970. The proximal channel portion 2910 includes a proximal end 2902, a distal end 2904, and an elongate channel 2906. The cartridge jaw 2900 defines a longitudinal axis $LA_2$ extending along a central axis of the cartridge jaw 2900.

A slot 2914 extends along a portion of the proximal channel portion 2910, and a slot 2916 extends along a portion of the distal portion 2970. The slots 2914, 2916 are aligned when the distal portion 2970 is mated with the proximal channel portion 2910, which corresponds to a closed position of the cartridge jaw 2900. When the staple cartridge 2820 is installed within the cartridge jaw 2900, the slot 2826 defined through the cartridge body of the staple cartridge 2820 can be aligned with the slots 2914 and 2916.

The cartridge jaw 2900 depicted in FIGS. 16 and 17 is in the open position, which can also be referred to as an unlocked or unengaged position. The closed position is when a distal face 2912 of the proximal channel portion 2910 is mated against a proximal face 2972 of the distal portion 2970. The channel 2976 of the distal portion 2970 matches the elongate channel 2906 of the proximal channel portion 2910 to form the full elongate channel of the cartridge jaw 2900 when in the closed position. In various instances, the distal portion 2970 may complete the lug-receiving recesses 2908a, 2908b, when the cartridge jaw 2900 is in the closed position. The lug-receiving recesses 2908a, 2908b may be located on both sides of the proximal channel portion 2910 at the distal end 2904. Lug-receiving recesses 2978a, 2978b in the distal portion 2970 may match with the recesses 2908a, 2908b of the proximal channel portion 2910 forming complete lug-receiving recesses for the detents or pan bumps 2830 on the staple cartridge 2820. When the staple cartridge 2820 is seated in the cartridge jaw 2900 and the cartridge jaw 2900 is in the closed position, the pan bumps 2830 rest inside of the completed recesses formed by the recesses 2908a, 2908b, 2978a, and 2978b.

Referring primarily to FIG. 17, the distal portion 2970 is pivotably attached to the proximal channel portion 2910. The distal portion 2970 may be pivotably attached with a torsion spring 2990. The torsion spring 2990 is attached to the proximal channel portion 2910 at a first end 2994 and attached to the distal portion 2970 at a second end 2992. The attachment of the torsion spring 2990 could be made by any means that solidly attaches the arms of the torsion spring 2990 to one of the proximal channel portion 2910 and distal portion 2970 (e.g. embedded). In some instances, the distal end 2904 could be designed to receive the second end 2992 of the torsion spring, and the proximal channel portion 2910 could be designed to receive the first end 2994 of the torsion spring. In some instances, the torsion spring ends 2992, 2994 could be glued or otherwise fastened in their attachment locations to add additional support.

Referring still to FIG. 17, the torsion spring 2990 may apply a force to bias the distal portion 2970 towards the closed position. Stated another way, the torsion spring 2990 may apply a force to pivot the distal portion 2970 towards the closed position. To place the cartridge jaw 2900 in the open position, the force applied by the spring needs to be overcome to move the distal portion 2970 to the open position. In some instances, snap features and a torsion spring may be required to hold the cartridge jaw 2900 in the closed position. In other instances, the torsion spring alone may be capable of holding the cartridge jaw 2900 in the closed position.

Figure 18:
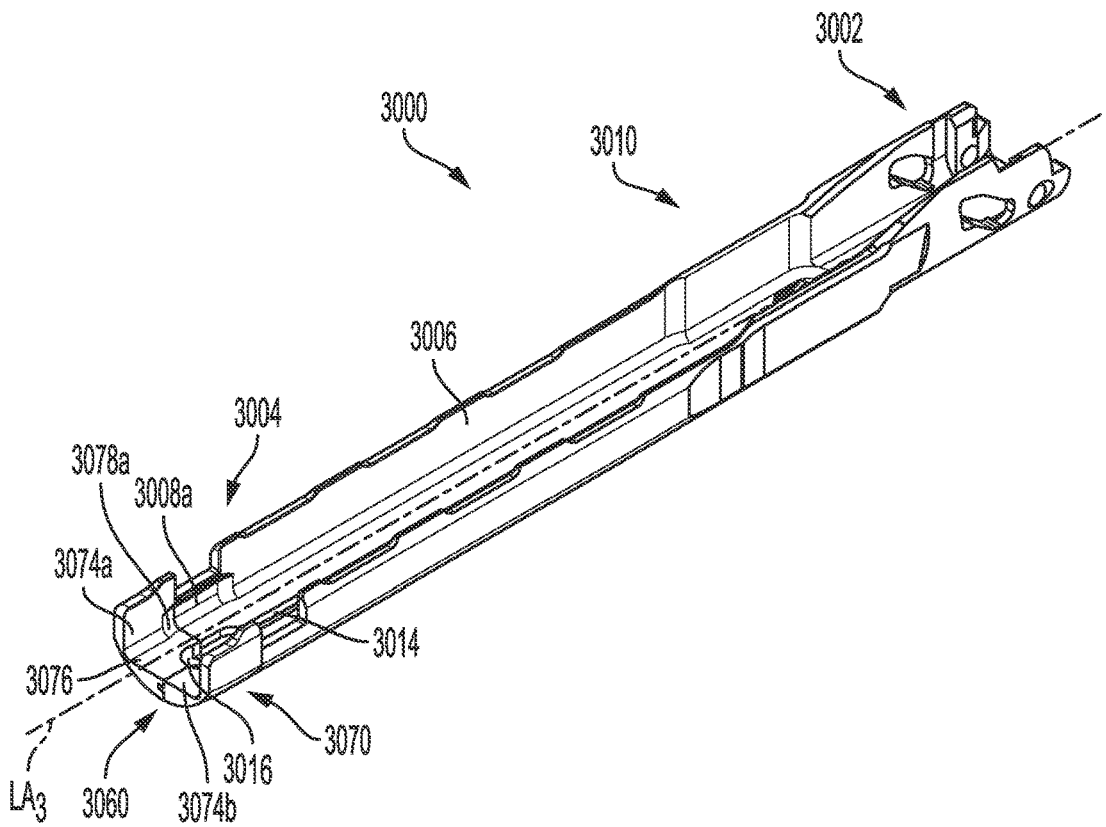
FIG. 18 is a perspective view of a cartridge jaw with a two-piece distal portion in a closed position, according to at least one aspect of the present disclosure.

FIGS. 18-21 show a cartridge jaw 3000 with a two-piece distal portion 3070. The cartridge jaw 3000 is similar in many aspects to the cartridge jaws 2800, 2900; various differences are further described herein. FIG. 18 shows the cartridge jaw 3000 in the closed position, which could also be referred to as a locked or engaged position. The cartridge jaw 3000 includes a proximal channel portion 3010 and a distal portion 3070. The proximal channel portion 3010 includes a proximal end 3002, a distal end 3004, and an elongate channel 3006. The cartridge jaw 3000 defines a longitudinal axis $LA_3$ going down the middle or central portion of the cartridge jaw 3000. A slot 3014 extends along a portion of the proximal channel portion 3010, and a bifurcated slot 3016 extends along a portion of the distal portion 3070. The slots 3014, 3016 are aligned when the distal portion 3070 is mated with the proximal channel portion 3010, which corresponds to a closed position of the cartridge jaw 3000. When the staple cartridge 2820 is installed within the cartridge jaw 3000, the slot 2826 defined through the cartridge body of the staple cartridge 2820 can be aligned with the slots 3014 and 3016.

Figure 21:
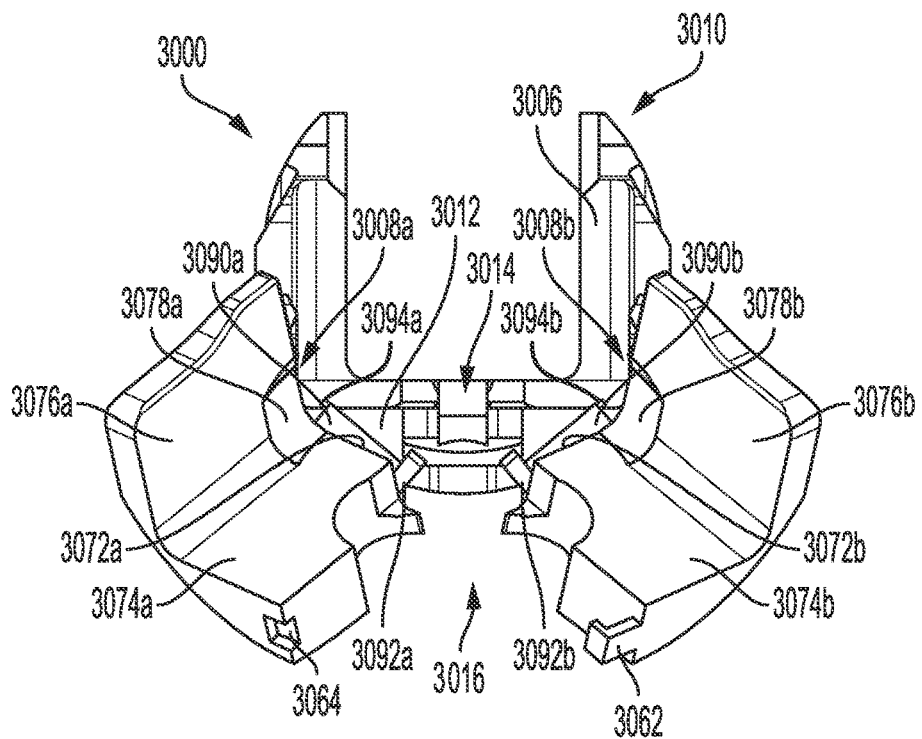
FIG. 21 is a front view of the two-piece distal portion of the cartridge jaw of FIG. 18 in the open position, according to at least one aspect of the present disclosure.

Referring to FIG. 18, the two pieces 3074a, 3074b of the distal portion 3070 can come together by any means that allow the two pieces 3074a, 3074b to attach and detach from each other. In some instances, the two pieces 3074a, 3074b snap together with a snap feature 3060 to form the shape of the distal portions 2870, 2970, for example. The snap feature 3060 may comprise a male snap feature 3062 and a female snap feature 3064, as best seen in FIG. 21. These two snap features 3062, 3064 come together and hold the two pieces 3074a, 3074b together to place the distal portion 3070 into a one piece configuration defining a portion of the elongate channel for receiving the staple cartridge 2820 therein. The distal portion 3070 can be attached to the proximal channel portion 3010 to place the cartridge jaw 3000 in the closed position. In various instances, pivotal movement of the two pieces 3074a, 3074b of the distal portion 3070 into the closed position, can move the male snap feature 3062 and the female snap feature 3064 into locking alignment such that the snap feature 3060 locks the distal portion 3070 into the closed position upon placement in the closed position.

In the closed position, two distal portion faces 3072a, 3072b are mated against the proximal channel portion face 3012. Also, in the closed position, the two channel sidewalls 3076a, 3076b form sidewalls of the distal portion 3070 to match with the elongate channel 3006 of the proximal channel portion 3010 creating the full elongate channel of the cartridge jaw 3000. In the closed position, the lug-receiving recess 3008a completes the lug-receiving recess 3078a and the lug-receiving recess 3078b completes the lug-receiving recess 3008b. Lug-receiving recesses 3078a, 3078b of the distal portion 3070 match with the recesses 3008a, 3008b of the proximal channel portion 3010 forming complete lug-receiving recesses for the detents or pan bumps 2830 on the staple cartridge 2820. When the staple cartridge 2820 is seated in the cartridge jaw 3000 and the cartridge jaw 3000 is in the closed position, the pan bumps 2830 rest inside of the completed recesses formed by the recesses 3008a, 3008b, 3078a, and 3078b.

Figure 19:
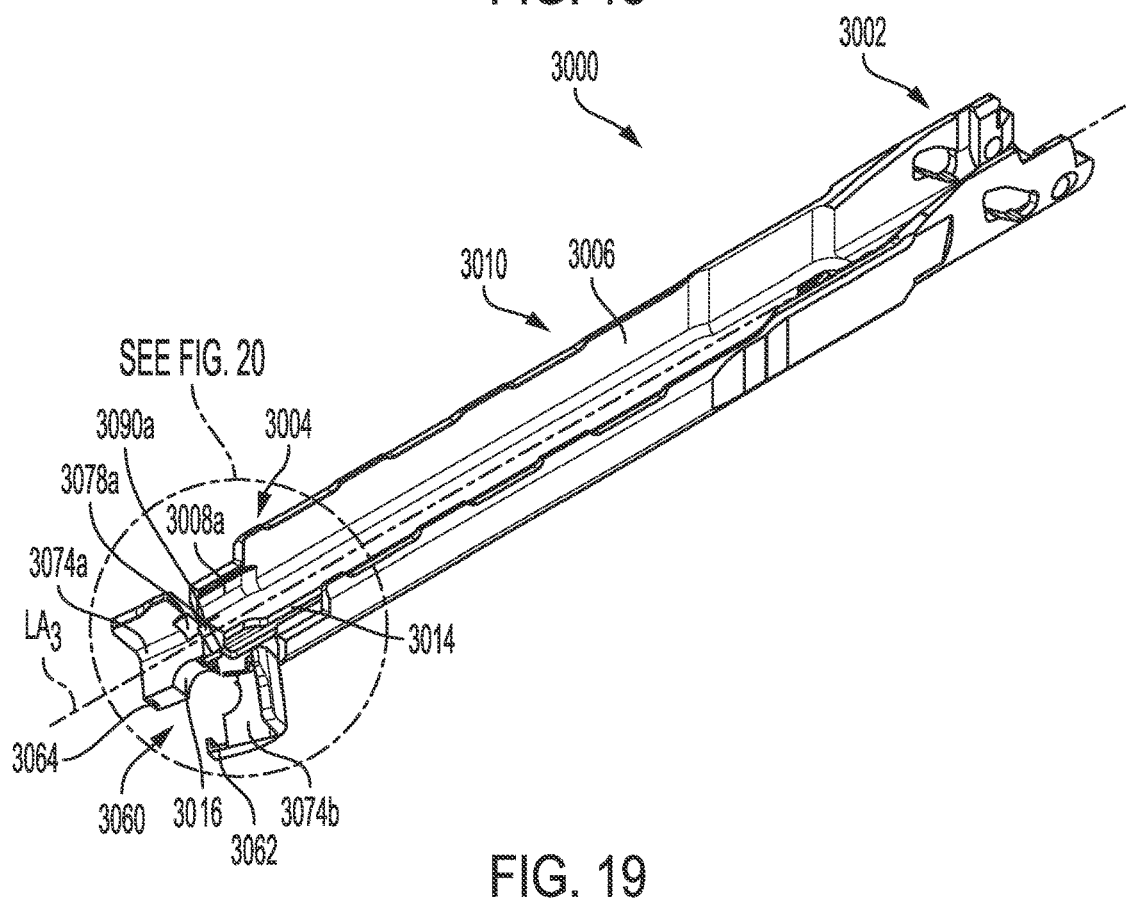
FIG. 19 is a perspective view of the cartridge jaw of FIG. 18 with the two-piece distal portion in an open position, according to at least one aspect of the present disclosure.
Figure 20:
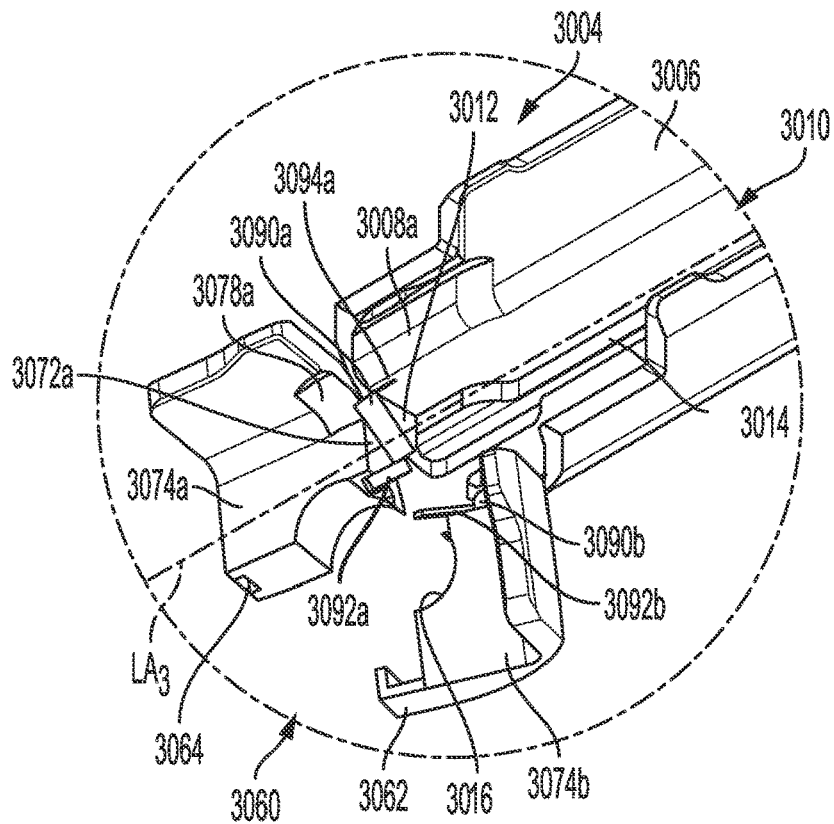
FIG. 20 is a detailed view of the two-piece distal portion of the cartridge jaw of FIG. 18 in the open position, according to at least one aspect of the present disclosure.

FIGS. 19-21 show the cartridge jaw 3000 in the open position, which could also be referred to as an unlocked or unengaged position. FIG. 20 provides a detailed view of the distal end of the cartridge jaw 3000 and FIG. 21 provides a front view of the cartridge jaw 3000 in the opened position. The two pieces 3074a, 3074b of the distal portion 3070 are pivotably attached to the proximal channel portion 3010. For example, the two pieces 3074a, 3074b are pivotably attached with torsion springs 3090a, 3090b. The torsion springs 3090a, 3090b are substantially similar to the torsion spring 2990 in how they operate and how they are attached. The torsion spring 3090a is attached to the proximal channel portion 3010 at a first end 3094a and attached to the distal portion piece 3074a at a second end 3092a. The torsion spring 3090b is likewise attached to the proximal channel portion 3010 at a first end 3094b and attached to the distal portion piece 3074b at a second end 3092b. The attachment of the torsion springs 3090a, 3090b could be made by any means that solidly attaches the torsion springs 3090a, 3090b to the proximal channel portion 3010 and distal portion pieces 3074a, 3074b. In some instances, the distal portion pieces 3074a, 3074b could be designed to receive the second ends 3092a, 3092b of the torsion springs 3090a, 3090b, and the proximal channel portion 3010 could be designed to receive the first ends 3094a, 3094b of the torsion springs 3090a, 3090b. In some instances, the torsion spring ends 3092a, 3092b, 3094a, 3094b could be glued or fastened in their attachment locations to provide additional support.

Referring to FIG. 21, the torsion spring 3090a may apply a force to bias the distal portion piece 3074a laterally inward to the closed position. Stated another way, the torsion spring 3090a may apply a force to move the distal portion piece 3074a towards the closed position. Additionally, the torsion spring 3090b may apply a force to bias the distal portion piece 3074b towards the closed position. Stated another way, the torsion spring 3090b may apply a force to move the distal portion piece 3074b towards the closed position. To place the cartridge jaw 3000 fully into the closed position, distal portion pieces 3074a, 3074b are attached together. To place the cartridge jaw 3000 in the open position, the distal portion pieces 3074a, 3074b are detached from each other. The force applied by the springs 3090a, 3090b may need to be overcome to move the distal portion pieces 3074a, 3074b to the open position. In some instances, a combination of snap features and torsion springs may be used to hold the distal portion 3070 against the cartridge jaw 3000 maintaining the closed position. In other instances, the torsion springs 3090a, 3090b alone may be capable to hold the distal portion 3070 against the cartridge jaw 3000 and maintaining the closed position.

In various instances, the two-piece distal portion 3070 can provide attachment mechanisms for each portion that are offset from the longitudinal axis $LA_3$. In such instances, the longitudinal slot formed in the proximal channel portion and the distal portion (slot 3014 and slot 3016) can be unobstructed and a firing member can pass from the slot 3014 into the slot 3016 in certain instances.

Examples

Various aspects of the subject matter described herein are set out in the following numbered examples.

Example 1—A surgical end effector, comprising a cartridge jaw. The cartridge jaw comprising a proximal channel portion extending along a longitudinal axis, and a distal portion movable relative to the proximal channel portion between an open position and a closed position. The surgical end effector further comprising a staple cartridge removably seated in the cartridge jaw, wherein the staple cartridge is configured to slide along the longitudinal axis into the proximal channel portion of the cartridge jaw when the distal portion is in the open position.

Example 2—The surgical end effector of Example 1, wherein the staple cartridge is configured to slide proximally along the longitudinal axis into the proximal channel portion.

Example 3—The surgical end effector of Examples 1 or 2, wherein, in the closed position, the distal portion is configured to hold the staple cartridge in the proximal channel portion.

Example 4—The surgical end effector of Examples 1, 2, or 3, further comprising snap features intermediate the distal portion and the proximal channel portion.

Example 5—The surgical end effector of Examples 1, 2, 3, or 4, further comprising a spring configured to bias the distal portion toward the closed position.

Example 6—The surgical end effector of Examples 1, 2, 3, 4, or 5, wherein the distal portion comprises: a first distal portion pivotably mounted to the proximal channel portion at a first pivot joint, and a second distal portion pivotably mounted to the proximal channel portion at a second pivot joint.

Example 7—The surgical end effector of Example 6, wherein the first pivot joint comprises a torsion spring.

Example 8—A surgical stapling assembly, comprising a channel. The channel comprising a proximal channel portion extending distally along a longitudinal axis, and a distal channel portion movably coupled to the proximal channel portion. The surgical stapling assembly further comprises a replaceable staple cartridge configured to slide into the proximal channel portion along the longitudinal axis to an installed position in the channel.

Example 9—The surgical stapling assembly of Example 8, wherein the distal channel portion is configured to pivot between a locked position, in which the distal channel portion extends distally along the longitudinal axis, and an unlocked position, in which the distal channel portion extends along a transverse axis relative to the longitudinal axis.

Example 10—The surgical stapling assembly of Example 9, wherein, in the locked position, the distal channel portion is configured to secure the replaceable staple cartridge in the proximal channel portion.

Example 11—The surgical stapling assembly of Examples 8, 9 or 10, further comprising snap features intermediate the distal channel portion and the proximal channel portion.

Example 12—The surgical stapling assembly of Examples 8, 9, 10, or 11, further comprising snap features intermediate the replaceable staple cartridge and the proximal channel portion.

Example 13—The surgical stapling assembly of Examples 9, 10, 11, or 12, further comprising a spring configured to bias the distal channel portion toward the locked position.

Example 14—The surgical stapling assembly of Examples 8, 9, 10, 11, 12, or 13, wherein the distal channel portion comprises a first distal portion pivotably mounted to the proximal channel portion at a first pivot joint comprising a first torsion spring, and a second distal portion pivotably mounted to the proximal channel portion at a second pivot joint comprising a second torsion spring.

Example 15—A method of replacing a staple cartridge in a cartridge jaw of a surgical end effector of a robotic surgical tool. The method comprising moving a distal portion of the cartridge jaw from a closed position to an open position, sliding a first staple cartridge distally out of the cartridge jaw, sliding a second staple cartridge proximally into the cartridge jaw, and moving the distal portion of the cartridge jaw to the closed position to secure the second staple cartridge in the cartridge jaw.

Example 16—The method of Example 15, wherein moving the distal portion from the cartridge jaw from the closed position to the open position comprises overcoming a spring force.

Example 17—The method of Examples 15 or 16, wherein the distal portion comprises a first distal portion and a second distal portion, and wherein moving the distal portion of the cartridge jaw from the closed position to the open position comprises pivoting the first distal portion laterally away from the second distal portion.

Example 18—The method of Example 17, wherein moving the distal portion of the cartridge jaw to the closed position comprises pivoting the second distal portion laterally toward the first distal portion.

Example 19—The method of Examples 17 or 18, wherein moving the distal portion of the cartridge jaw to the closed position comprises latching the first distal portion to the second distal portion.

Example 20—The method of Examples 15, 16, 17, 18, or 19, wherein sliding the second staple cartridge proximally into the cartridge jaw further comprises overcoming a friction fit connection.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material. In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical end effector, comprising:
   a cartridge jaw, comprising:
      a proximal channel portion extending along a longitudinal axis, wherein the proximal channel portion comprises proximal sidewalls flanking the longitudinal axis; and
      a distal channel portion movable relative to the proximal channel portion between an open position and a closed position, wherein the distal channel portion comprises distal sidewalls, and wherein, in the closed position, the proximal channel portion and the distal channel portion cooperatively define an elongate channel; and
   a staple cartridge, wherein, in the open position, the staple cartridge is configured to slide along the longitudinal axis into the proximal channel portion, and wherein, in the closed position, the staple cartridge is removably seated in the elongate channel intermediate the proximal sidewalls and intermediate the distal sidewalls.

2. The surgical end effector of claim 1, wherein the staple cartridge is configured to slide proximally along the longitudinal axis into the proximal channel portion.

3. The surgical end effector of claim 1, wherein, in the closed position, the distal channel portion is configured to hold the staple cartridge in the proximal channel portion.

4. The surgical end effector of claim 1, further comprising snap features intermediate the distal channel portion and the proximal channel portion.

5. The surgical end effector of claim 1, further comprising a spring configured to bias the distal channel portion toward the closed position.

6. The surgical end effector of claim 1, wherein, in the closed position, the proximal channel portion and the distal channel portion form a recess in the elongate channel, and wherein the staple cartridge comprises a protrusion dimensioned to fit inside the recess.

7. The surgical end effector of claim 1, wherein, in the closed position, the staple cartridge extends distally past the distal channel portion.

8. A surgical end effector, comprising:
a cartridge jaw, comprising:
a proximal channel portion extending along a longitudinal axis; and
a distal portion movable relative to the proximal channel portion between an open position and a closed position, wherein the distal portion comprises:
a first distal portion pivotably mounted to the proximal channel portion at a first pivot joint; and
a second distal portion pivotably mounted to the proximal channel portion at a second pivot joint; and
a staple cartridge removably seated in the cartridge jaw, wherein the staple cartridge is configured to slide along the longitudinal axis into the proximal channel portion of the cartridge jaw when the distal portion is in the open position.

9. The surgical end effector of claim 8, wherein the first pivot joint comprises a torsion spring.

10. A surgical stapling assembly, comprising:
a channel, comprising:
a proximal channel portion extending distally along a longitudinal axis, wherein the proximal channel portion comprises proximal sidewalls; and
a distal channel portion pivotably coupled to the proximal channel portion, wherein the distal channel portion comprises distal sidewalls; and
a replaceable staple cartridge configured to slide into the proximal channel portion along the longitudinal axis to an installed position in the channel, and wherein, in the installed position, the replaceable staple cartridge is seated in the channel intermediate the proximal sidewalls and intermediate the distal sidewalls.

11. The surgical stapling assembly of claim 10, wherein, in the installed position, the proximal channel portion and the distal channel portion form a recess in the channel, and wherein the replaceable staple cartridge comprises a protrusion dimensioned to fit inside the recess.

12. The surgical stapling assembly of claim 10, wherein, in the installed position, the replaceable staple cartridge extends distally past the distal channel portion.

13. A surgical stapling assembly, comprising:
a channel, comprising:
a proximal channel portion extending distally along a longitudinal axis; and
a distal channel portion movably coupled to the proximal channel portion; and
a replaceable staple cartridge configured to slide into the proximal channel portion along the longitudinal axis to an installed position in the channel;
wherein the distal channel portion is configured to pivot between a locked position, in which the distal channel portion extends distally along the longitudinal axis, and an unlocked position, in which the distal channel portion extends along a transverse axis relative to the longitudinal axis.

14. The surgical stapling assembly of claim 13, wherein, in the locked position, the distal channel portion is configured to secure the replaceable staple cartridge in the proximal channel portion.

15. The surgical stapling assembly of claim 13, further comprising snap features intermediate the distal channel portion and the proximal channel portion.

16. The surgical stapling assembly of claim 13, further comprising snap features intermediate the replaceable staple cartridge and the proximal channel portion.

17. The surgical stapling assembly of claim 13, further comprising a spring configured to bias the distal channel portion toward the locked position.

18. The surgical stapling assembly of claim 13, wherein the distal channel portion comprises:
a first distal portion pivotably mounted to the proximal channel portion at a first pivot joint comprising a first torsion spring; and
a second distal portion pivotably mounted to the proximal channel portion at a second pivot joint comprising a second torsion spring.

* * * * *